Figure 2A:
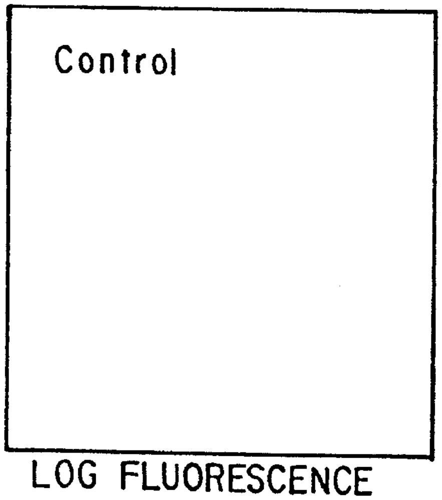
Figure 2B:
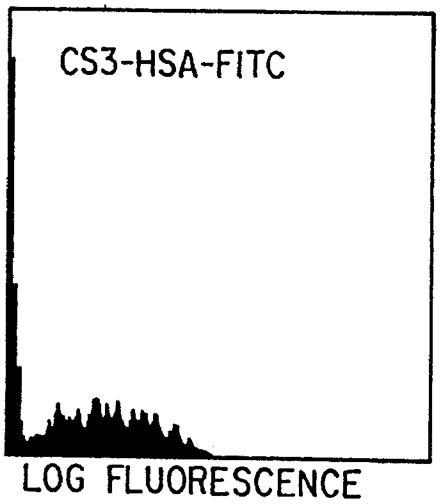
Figure 2C:
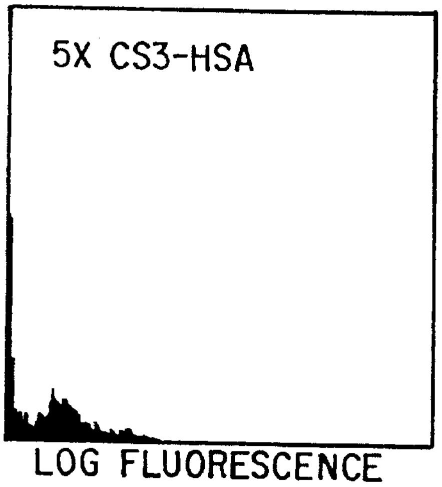
Figure 2D:
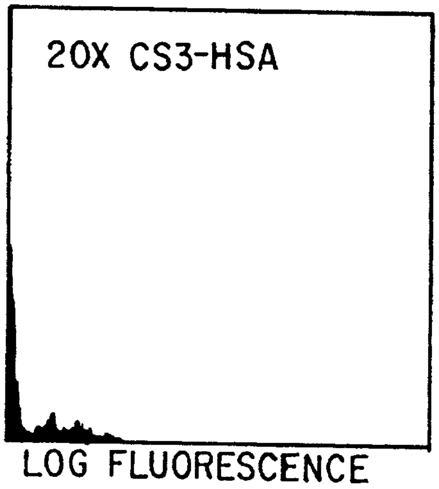
Figure 2E:
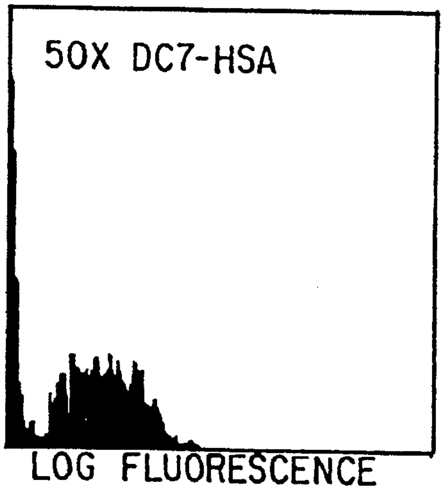

US005567805A

United States Patent [19]

[11] Patent Number: 5,567,805

[45] Date of Patent: Oct. 22, 1996

Henderson et al.

[54] THE CELLULAR RECEPTOR FOR THE CS3 PEPTIDE OF HUMAN IMMUNODEFICIENCY VIRUS

[75] Inventors: Lee A. Henderson; David H. Coy; Robert F. Garry, Jr., all of New Orleans, La.

[73] Assignee: Administrators of the Tulane Educational Fund, New Orleans, La.

[21] Appl. No.: 302,228

[22] Filed: Sep. 7, 1994

Related U.S. Application Data

[63] Continuation of Ser. No. 68,562, May 27, 1993, abandoned, which is a continuation of Ser. No. 626,652, Dec. 12, 1990, abandoned, which is a continuation-in-part of Ser. No. 592,016, Oct. 2, 1990, abandoned, which is a continuation of Ser. No. 491,137, Mar. 9, 1990, abandoned.

[51] Int. Cl.[6] .................... C07K 14/435

[52] U.S. Cl. .................... 530/350; 530/326; 435/5

[58] Field of Search .................... 435/5, 974; 530/326, 530/350

[56] References Cited

U.S. PATENT DOCUMENTS 4,822,606 4/1989 Snyderman et al. .................... 424/88

FOREIGN PATENT DOCUMENTS 88312216 12/1988 European Pat. Off. .
8805783 8/1988 WIPO .

OTHER PUBLICATIONS

Tsudo et al, PNAS. USA. 83. 9694–9698. 1986.
Garry, Aids, 3.(11).683–694(1989).
Gartner et al., Science 233:215–219 (1986).
Wainberg et al., Immunol. 54:1 (1985).
Pahwa et al., Proc. Nat'l Acad. Sci. 82:8198–8202 (1985).
Nair et al., Proc. Nat'l Acad. Sci. USA 85:6498–6502 (1988).
Sodroski et al., Nature 322:470–474 (1986).
Lifson et al., Nature 323:725–728 (1986).
Stevenson et al., Cell 53:483–496 (1988).
Smith et al., Science 238:1704–1707 (1987).
Fisher et al., Nature 331:76–78 (1988).
Lifson et al., Science 241:712–716 (1988).
Nara et al., Proc. Nat'l Acad, Sci. USA 86:7139–7143 (1989).
Hayashi et al., Arch. Virol. 105:129–135 (1989).
Chao et al., J. Biol. Chem. 264:5812–5817 (1989).
Billich et al., J. Biol. Chem. 263:17905–17908 (1988).
Moore et al., Biochem. Biophys. Res. Commun. 159:420–425 (1989).
Moore et al., Immunopharmacol. 16:181–189 (1988).
Cauda et al., Cell Immunol. 115:57–65 (1988).
Ruegg et al., J. Virol. 63:3257–3260 (1989).
Chanh et al., Cell Immunol. 111:77–86 (1988).
Cianciolo et al., Immunol. Lett. 19:7–14 (1988).
Rusche et al., Proc. Nat'l Acad. Sci. USA 85:3198–3208 (1988).
Dalgleish et al. Virology 165:209–215 (1988).
Dalgleish et al., UCLA Symposia on Mol. & Cell. Biochem. Supp. 13B at p. 288 (1989).
Starcich et al., Cell 45:637–648 (1986).
Klutzman and Gluckman, Immunol. Today 7:291–296 (1986).
Klasse et al., Proc. Nat'l Acad. Sci. USA 85:5225–5229 (1988).
Tenin, Rev. Inf. Dis. 10:399–405 (1988).
Fisher et al., Science 233:655–659 (1986).

*Primary Examiner*—Christine M. Nucker
*Assistant Examiner*—Jeffrey Stucker
*Attorney, Agent, or Firm*—Brumbaugh, Graves, Donohue & Raymond

[57] ABSTRACT

The present invention relates to methods of inhibiting HIV-mediated cell killing which comprises inhibiting the interaction between the CS3 region and viral gp41 and its receptor on the surface of lymphocytes. The invention provides for methods which employ peptides, peptide derivatives, or antibodies to inhibit the CS3/CS3 receptor interaction. In addition, the invention also relates to the CS3 receptor.

The present invention is based in part on the discovery that a CS3 specific cellular receptor is widely distributed on human lymphocytes and forms a 108 kd complex with CS3-HSA peptide conjugate. It was further discovered that CS3 peptide effectively blocks HIV mediated cell infection and killing. Therefore, the present invention provides for methods of treatment and prophylaxis of HIV infection as well as a means for better understanding the physiology of acquired immunodeficiency syndrome (AIDS).

5 Claims, 23 Drawing Sheets

```
BH10   TCAAATATTACAGGGCTGCTGTTAACAAGAGATGGTGGT   AATAGCAACAATGAGTCC
       SerAsnIleThrGlyLeuLeuLeuThrArgAspGlyGly   AsnSerAsnAsnGluSer
ARV2   ---------------------------------------ACA---CTA-CT-----CA--
                                              Thr   ValThr   AspThr
LAVIA  ---------------------------------------   ----A--------G----
                                                    Asn      Gly
WMJI   ---------------------------------------   -------G--GCAG-GAA
                                                       SerSerArgGlu
HATJ   --------------------A--------------G---GAGG---CA-CT---ACTA-A
                                              GluAspThrThr   ThrThr

BH10   GAGATCTTCAGACCTGGAGGAGGAGATATGAGGGACAATTGGAGAAGTGAATTATATAAA  1476
       GluIlePheArgProGlyGlyGlyAspMetArgAspAsnTrpArgSerGluLeuTyrLys
ARV2   ---C--------------------------------------------------------
          Val
LAVIA  ------------------------------------------------------------

WMJ1   ------------------------A-----------------------------------
                               Asn
HATJ   -------------T----------A-----------------------------------
                    Leu        Asn
```

FIG. 1A

```
                    EXTRACELLU-
BH10    TATAAAGTAGTAAAAATTGAACCATTAGGAGTAGCACCACCAAGGCAAAGAGAAGAGTG
        TyrLysValValLysIleGluProLeuGlyValAlaProThrLysAlaLysArgArgVal
ARV2    ------------A-----------------------------A------------------
                    Ile                                        Ile
LAVIA   ------------[ ]----------------------------------------------
WMJ1    ------------[ ]----------------------------------------------
HATJ    --------G--------G-----------------------[ ]T-G--------------
                    Arg                                        Arg

        -LAR REGION----          TRANSMEMBRANE REGION
BH10    GTGCAGAGAGAAAAAAGAGCAGTGGGAA  TAGGAGCTTGTTCCTTGGGTTCTTGGGA  1593
        ValGlnArgGluLysArgAlaValGly   IleGlyAlaLeuPheLeuGlyPheLeuGly
ARV2    ------[ ]-----------------------TAG---A--------------------
                                        IleVal  Met
LAVIA   ------[ ]---------------------------------------------------
WMJ1    ------[ ]---------------GCAA------A-------------------------
                                Ala       Met
HATJ    ------[ ]---------------CAA-------A-------------------------
                                Thr       Met
```

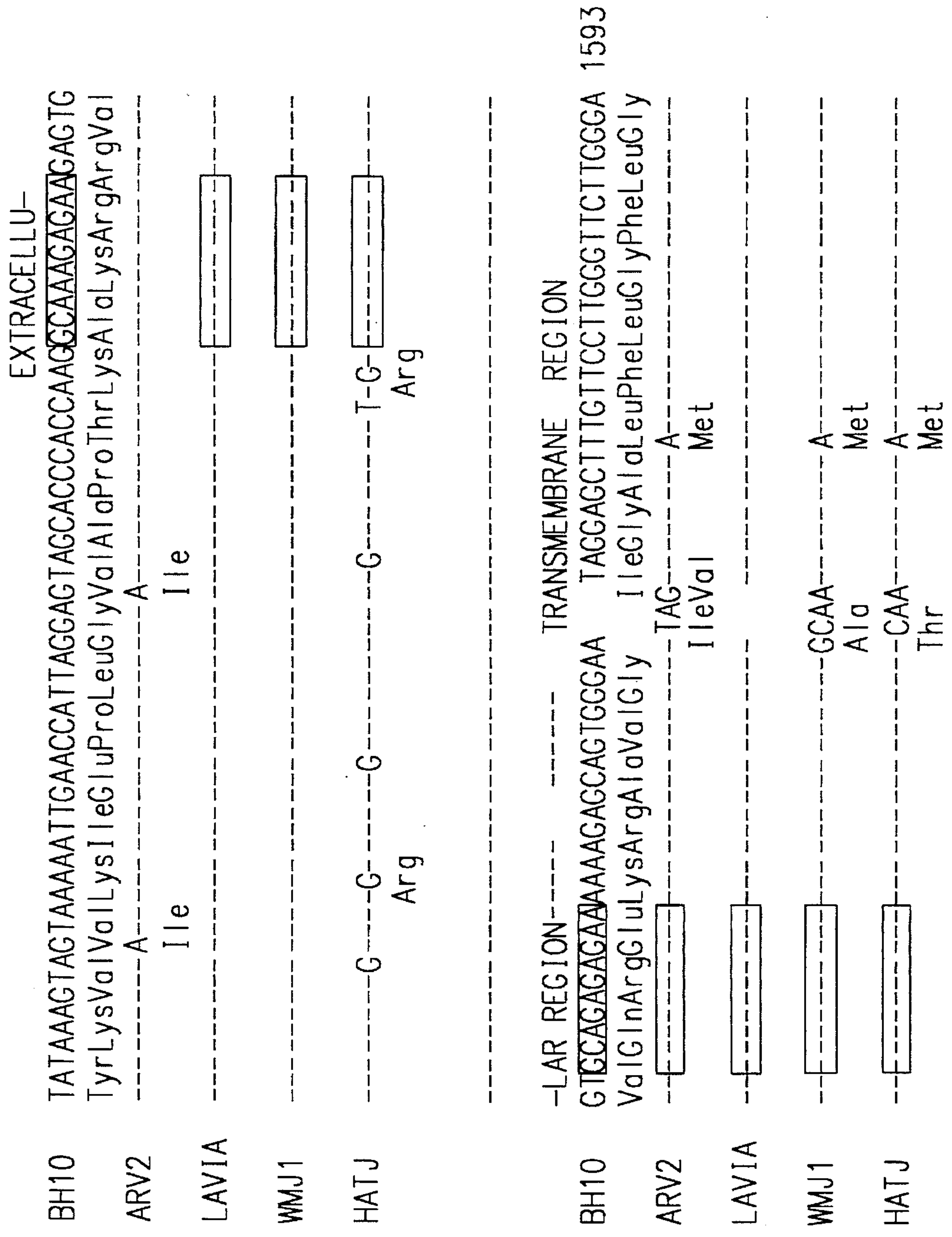

FIG.1B

```
BH10    GCAGCAGGAAGCACTATGGGCGCAGCGTCAATGACGCTGACGGTACAGGCCAGACAATTA
       AlaAlaGlySerThrMetGlyAlaAlaSerMetThrLeuThrValGlnAlaArgGlnLeu
ARV2    -------------------------T----T-----------------------------
                                Val   Leu
LAVIA   ------------------------CG----------------------------------
                                Arg
WMJ1    ------------------------------C-----------------------------
                                      Leu
HATJ    -------------------------GC-----A-----A----------------C---
                                Gly   Ile                     His

BH10    TTGTCTGGTATAGTGCAGCAGCAGAACAATTTGCTGAGGGCTATTGAGGCGCAACAGCAT 1713
        LeuSerGlyIleValGlnGlnGlnAsnAsnLeuLeuArgAlaIleGluAlaGlnGlnHis
ARV2    -----------------A--------------------------------------A---
LAVIA   ------------------------------------------------------------
WMJ1    -----------------A------------------------------------------
HATJ    -----------------A-----A------------------------------------
```

FIG. 1C

```
BH10   CTGTTGCAACTCACAGTCTGGGGCATCAAGCAGCTCCAGGCAAGAATCCTGGCTGTGGAA
       LeuLeuGlnLeuThrValTrpGlyIleLysGlnLeuGlnAlaArgIleLeuAlaValGlu
ARV2   ---------------------------------------------G--------------
                                                    Val
LAVIA  ------------------------------------------------------------

WMJ1   --------------G--------------A---------------G--------------
                                                    Val
HATJ   --------------G--------------A---------------G--------------
                                                    Val

BH10   AGATACCTAAAGGATCAACAGCTCCTGGGGATTTGGGGTTGCTCTGGAAAACTCATTTGC 1833
       ArgTyrLeuLysAspGlnGlnLeuLeuGlyIleTrpGlyCysSerGlyLysLeuIleCys
ARV2   ----------G---------------A---------------------------------
                Arg
LAVIA  ------------------------------------------------------------

WMJ1   ----------G---------------A---------------------------------
                Arg
HATJ   ----------G---------------A--A--------A---------------------
                Arg
```

FIG. 1D

```
BH10   ACCACTGCTGTGCCTTGGAATGCTAGTTGGAGTAATAAATCTCTGGAACAGATTTGGAAT
       ThrThrAlaValProTrpAsnAlaSerTrpSerAsnLysSerLeuGluGlnIleTrpAsn
ARV2   ------------------------------------------------G-C------G--
                                                       Asp      Asp
LAVIA  ------------------------------------------------------------

WMJ1   ------A-------------C---------------------A----T--A---------
             Thr                                 MetAsp
HATJ   ------A--------------------------------------A-TAT----------
             Thr                                    AsnMet

BH10   AACATGACCTGGATGGAGTGGGACAGAGAAATTAACAATTACACAAGCTTAATACACTCC 1953
       AsnMetThrTrpMetGluTrpAspArgGluIleAsnAsnTyrThrSerLeuIleHisSer
ARV2   ---------------C-------A---------G------------A-AC----T--A--
                      Gln   Glu         Asp         AsnThr   TyrThr
LAVIA  --------------------------------------------------------T---

WMJ1   -----------------------A---------G--------------------T--AA-
                            Glu         Asp                  TyrAsn
HATJ   ---------------C-------A---------G-----------G--A-----T--AA-
                      Gln   Glu         Asp         GlyIle   TyrAsn
```

FIG. 1E

```
BH10   TTAATTGAAGAATCGCAAAACCAGCAAGAAAAGAATGAACAAGAATTATTGGAATTAGAT
       LeuIleGluGluSerGlnAsnGlnGlnGluLysAsnGluGlnGluLeuLeuGlyLeuAsp
ARV2   ---C-------------G-----A--------------------------A-----G---
          Leu
LAVIA  ------------------------------------------------------------

WMJ1   -----------------G--------------------------------A-----G---

HATJ   ---C-------------G--------------------------------------G---
          Leu

BH10   AAATGGGCAAGTTGTGTGGAATTGGTTAACATAACAAATTGGCTGTGGTATATAAAATTA 2073
       LysTrpAlaSerLeuTrpAsnTrpPheAsnIleThrAsnTrpLeuTrpTyrIleLysLeu
ARV2   --G-------------------------G---------C-----------------GA--
                                  Ser                            Ile
LAVIA  ---------------------------------------------------------A--
                                                                 Ile
WMJ1   --G---------C--------------TC---------C------------------A--
                   Leu            Ser                            Ile
HATJ   ----------A----------------G--------C-A----------------G-A--
                Asn               Asp      Gln                ArgIle
```

FIG. 1F

```
BH10    TTCATAATGATAGTAGGAGGCTTGGTAGGTTTAAGAATAGTTTTTGCTGTACTTTCTGTA
        PheIleMetIleValGlyGlyLeuValGlyLeuArgIleValPheAlaValLeuSerVal
ARV2    --------------------------------------------------G------A--
                                                                 Ile
LAVIA   ---------------------------------------------------------A--
                                                                 Ile
WMJ1    --T------------------------------------------AG----------A--
                                                     Ser         Ile
HATJ    ------------------------------C---A---------------G------A--
                                         Lys                     Ile

BH10    GTGAATAGAGTTAGGCAGGGATATTCACCATTATCGTTTCAGACCCACCTCCCAATCCCG 2293
        ValAsnArgValArgGlnGlyTyrSerProLeuSerPheGlnThrHisLeuProIlePro
ARV2    -----------------------C--------G--A----------G-------G-----
                                                     Arg      Val
LAVIA   -------------------------------------------------------C----
                                                              Thr
WMJ1    -----------------------C-----------A-------------------C----
                                                              Thr
HATJ    -----------------------C-----------A------------------GC----
                                                              Ala
```

FIG. 1G

```
BH10   AGGGGACCCGACAGGCCCGAAGGAATAGAAGAAGAAGGTGGAGAGAGAGACAGAGACAGA
       ArgGlyProAspArgProGluGlyIleGluGluGluGlyGlyGluArgAspArgAspArg
ARV2   --------------------C-----C---------------------------------
                         Asp
LAVIA  ------------------------------------------------------------

WMJ1   -------------------------C----------------------------------
                               Thr
HATJ   --------------------------C----G----------------------------
                                     Gly

BH10   TCCATTCGATTAGTGAACGGATCCTTAGCACTTATCTGGGACGATCTGCGGAGCCTGTGC 2313
       SerIleArgLeuValAsnGlySerLeuAlaLeuIleTrpAspAspLeuArgSerLeuCys
ARV2   ---G-----------G-T----T------------------A------------------
          Val         Asp   Phe               Glu
LAVIA  ------------------------------------------------------------

WMJ1   ---G-------G---C-T----T-------------------------------------
          Val         His   Phe
HATJ   ---GGCG-TGC------T----T---GA--------------------T---C-------
          GlyGlyAla         Phe    Thr                 TrpThr
```

FIG. 1H

```
BH10   CTCTTCAGCTACCACCGCTTGAGAGACTTACTCTTGATTGTAACGAGGATTGTGGAACTT
       LeuPheSerTyrHisArgLeuArgAspLeuLeuLeuIleValThrArgIleValGluLeu
ARV2   -------------G--------------------------C-G------C-------A--
                   Arg                        AlaAla   Thr      Ile
LAVIA  ------------------------------------------------------------

WMJ1   ------------------------------------------------------------

HATJ   AG------------------------------------A---GT----------------
       Ser                                       Val

BH10   CTGGGACGCAGGGGGTGGGAAGCCCTCAAATATTGGTGGAATCTCCTACAGTATTGGAGT 2433
       LeuGlyArgArgGlyTrpGluAlaLeuLysTyrTrpTrpAsnLeuLeuGlnTyrTrpSer
ARV2   -----G-A--------------------------------G------G----------T-
             His                              Ser               Ile
LAVIA  ------------------------------------------------------------

WMJ1   -----------------------------G-----------------G-----------C

HATJ   -----------------------------G-----------------G------------
```

FIG. 1I

```
BH10    CAGGAGCTAAAGAATAGTGCTGTTAGCTTGCTCAATGCCACAGCTATAGCAGTAGCTGAG
        GlnGluLeuLysAsnSerAlaValSerLeuLeuAsnAlaThrAlaIleAlaValAlaGlu
ARV2    -----A----------------------G------C------------------A-----
                                   Trp                        Thr
LAVIA   -----A--------------------------------------C---------------

WMJ1    A----A------------------G-G-----T-------TT------------------
        Lys                     Gly            Ile
HATJ    --------------------------------T---A-------A--------------A
                                            Thr

BH10    GGGACAGATAGGGTTATAGAAGTAGTACAAGGAGCTTATAGAGCTATTCGCCACATACCT 2552
        GlyThrAspArgValIleGluValValGlnGlyAlaTyrArgAlaIleArgHisIlePro
ARV2    -------------------------C----A------------------T--------A-
                                Ala   Arg               Leu      His
LAVIA   ------------------------------------G-----------------------
                                            Cys
WMJ1    ------------------------------A--ATC-G----------AT----------
                                      ArgIleCys         Ile
HATJ    ------------A------------C----A--AT-CT-------T---TT---------
                    Ile         Ala   ArgIleLeu      PheLeu
```

FIG. 1J

```
BH10    AGAAGAATAAGACAGGGCTTGGAAAGGATTTTGCTA  2589
        ArgArgIleArgGlnGlyLeuGluArgIleLeuLeu
ARV2    --------T------------------C--------
                                   Leu
LAVIA   ------------------------------------

WMJ1    ---------------------------GC-------
                                   Ala
HATJ    ---------------------------GC------G
                                   Ala
```

FIG. 1K

STEP 1
Incubate HIV with cells at 4°

STEP 2
Layer over silicon oil mixture;
Centrifuge at 15,000 X g for
1 minute

STEP 3
Rapidly freeze tube in liquid
nitrogen; Cut off tip containing
cell pellet.

STEP 4
Assay for HIV antigen by EIA

THE CELLULAR RECEPTOR FOR THE CS3 PEPTIDE OF HUMAN IMMUNODEFICIENCY VIRUS

This application is a continuation of U.S. application Ser. No. 08/068,562, filed May 27, 1993 (abandoned); which is a continuation of U.S. application Ser. No. 07/626,652, filed Dec. 12, 1990 (abandoned); which is a continuation-in-part of U.S. application Ser. No. 07/592,016 filed Oct. 2, 1990, now abandoned which in turn is a continuation of U.S. application Ser. No. 07/491,137, filed Mar. 9, 1990, (abandoned) the disclosures of which are incorporated herein by reference.

TABLE OF CONTENTS

Page
1. Introduction
2. Background Of The Invention
   2.1. Human Immunodeficiency Virus (HIV)
   2.2. Human Immunodeficiency Virus Inhibitory Peptides
3. Summary Of The Invention
   3.1. Abbreviations
4. Description Of The Figures
5. Detailed Description Of The Invention
   5.1. Peptides Of The Invention
   5.2. Antibodies Of The Invention
   5.3. Utility Of The Invention
6. Example: Expression Of CS3 Receptors On Lymphocytes
   6.1. Materials And Methods
   6.2. Results And Discussion
7. Example: Inhibition Of HIV-Mediated Cell Killing By CS3-HSA
   7.1. Materials And Methods
   7.2. Results And Discussion
8. Example: Characterization Of The CS3 Receptor
   8.1. Materials And Methods
   8.2. Results And Discussion
9. Example: CS3-HSA Blocks Infection By HIV
   9.1. Materials And Methods
   9.2. Results And Discussion
10. Example: CS3-HSA Inhibits Binding Of HIV To Cells
   10.1. Materials And Methods
   10.2. Results And Discussion
11. Example: CS3-HSA Upregulates Expression Of The CS3 Receptor And HLA-DR1
   11.1 Materials And Methods
   11.2. Results And Discussion
12. Example: Expression Of The CS3 Receptor On Various Cell Lines
13. Example: Development Of A New Assay Demonstrating The Mechanism Of CS3 Action
   13.1. Effects Of The CS3 Peptide On HIV Pathogenesis
   13.2. Distribution Of The CS3 Binding Domain
   13.3. Regulation Of CS3 Binding Domain Expression
14. Example: The CS3 Receptor Comprises Two Polypeptide Subunits

1. INTRODUCTION

The present invention relates to methods of inhibiting human immunodeficiency virus-mediated cell killing and infection which inhibit interaction between a viral protein and a novel specific cellular receptor.

2. BACKGROUND OF THE INVENTION

2.1. Human Immunodeficiency Virus

Human immunodeficiency virus (HIV) is a human retrovirus believed to be the causative agent of acquired immune deficiency syndrome (AIDS) and AIDS related complex (ARC). The HIV virion or virus particle is a sphere that is roughly 1000 angstrom units across. The particle is covered by a lipid bilayer membrane derived from the outer membrane of the infected host cell. Studding the viral membrane is an envelope glycoprotein which is synthesized as a precursor of 160 kd and subsequently processed into two glycoproteins: gp41 which spans the lipid bilayer, and gp120 which extends beyond the lipid bilayer. The envelope covers a core made up of proteins designated p24 and p18. The viral RNA is carried in the core, along with several copies of the enzyme, reverse transcriptase, which catalyzes the assembly of viral DNA.

The HIV genome contains three genes that encode the components of retrovirus particles: env (which codes for the envelope proteins), gag (which codes for the core proteins), and pol (which codes for reverse transcriptase). These three genes are flanked by stretches of nucleotides called long terminal repeats (LTRs). The LTRs include sequences that have a role in controlling the expression of viral genes. However, unlike other retroviruses, the genome of HIV includes at least five additional genes, three of which have known regulatory functions, and the expression of which is thought to have an impact on the pathogenic mechanisms exerted by the virus. The tat gene encodes a protein that functions as a potent trans-activator of HIV gene expression, and, therefore, plays an important role in the amplification of virus replication. The rev, or trs/art gene can upregulate HIV synthesis by a transacting antirepression mechanism; rev enables the integrated HIV virus to selectively produce either regulatory proteins or virion components. In contrast, the nef, or 3'-orf, gene appears to down-regulate virus expression by producing a cytoplasmic protein which, presumably via a second messenger, inhibits transcription of the HIV genome. The vif, or sor gene is not essential for virion formation, but is critical to the efficient generation of infectious virions and influences virus transmission in vitro. The pr, or R gene encodes an immunogenic protein of unknown function.

An important basis for the immunopathogenesis of HIV infection is believed to be the depletion of the helper/inducer subset of T lymphocytes, which express the CD4 antigen, resulting in profound immunosuppression. Viral killing of these immune cells is thought to be a major factor contributing to the crippling effect HIV has on the immune system. The envelope glycoprotein appears to play an important role in the entry of HIV into CD4 positive host cells. The gp120 portion has been shown to bind directly to the cellular CD4 receptor molecule, thereby producing HIV's tropism for host cells that express the CD4 receptor, e.g., T helper cells (T4 cells), macrophages, etc.

After HIV binds to the CD4 molecule, the virus is internalized and uncoated. Once internalized, the genomic RNA is transcribed into DNA by the enzyme reverse transcriptase. The proviral DNA is then integrated into the host chromosomal DNA and the infection may assume a "dormant" or latent phase. However, once activation occurs, the proviral DNA is transcribed. Translation and post translational processing results in virus assembly and budding of mature virions from the cell surface.

When active replication of virus occurs, the host CD4+ cell is usually killed, but some cells may persistently produce virus and are not killed. However, the precise mechanism by which HIV exerts its cytopathic effect is unknown, and in fact CD4 cell killing has been observed with exposure to inactivated virus. A number of mechanisms for the immunopathogenesis and cytopathic effect of HIV infection have been proposed: the accumulation of large amounts of unintegrated viral DNA in the infected cells; massive increase in permeability of the cell membrane when large amounts of virus bud off the cell surface; speculations that HIV may induce terminal differentiation of infected T4 cells, leading to a shortened life span. There is growing evidence that both the CD4 molecule and the virus envelope play a role in cytopathic effect in HIV infected cells by somehow promoting cell fusion. A prominent feature in the cytopathology of HIV infection is the formation of multinucleated syncytia formed by the fusion of as many as 500 cells which appear to be induced by the gp120/gp41 envelope proteins. In contrast, HIV-infected macrophages may continue to produce HIV without cytopathic effects for long periods of time; it is believed that the macrophage is a major reservoir for HIV and may be responsible for transporting virus into the central nervous system (Gartner et al., 1986, Science 233:215–219).

To date, there is no cure for AIDS. Vaccine trials are currently underway in an attempt to control the spread of the virus among the population. However, efforts at controlling the course of disease within an infected patient have been directed mainly towards the use of antiviral agents.

2.2. Human Immunodeficiency Virus Inhibitory Peptides

Wainberg et al. (1985, Immunol. 54:1) observed that the culture of normal human lymphocytes with either active or ultraviolet-light inactivated HTV-I appeared to suppress mitogen responsiveness. Similarly, Pahwa et al. (1985, Proc. Natl. Acad. Sci. U.S.A. 82:8189) found that detergent-disrupted HIV inhibited lymphocyte proliferation in response to mitogen stimulation as well as natural killer cell activity. It was suggested that peptides of the HIV genome provide immunoregulatory T and B-cell epitopes (Nair et al., 1988, Proc. Natl. Acad. Sci. U.S.A. 85:6498–6502).

The binding of gp120 to CD4 antigen has been associated not only with viral penetration of cell membranes, but to syncytia formation as well (Sodroski et al., 1986, Nature 322:470–474; Lifson et al., 1986, Nature 323:725–728; Stevenson et al., 1988, Cell 53:483–496). Smith et al. (1987, Science 238:1704–1707) observed that soluble CD4 antigen can block HIV infectivity by binding to viral particles before they encounter CD4 molecules embedded in cell membranes (see also Fisher et al., 1988, Nature 331:76–78). It has been reported that derivatives of CD4 peptides, such as benzylated derivatives, may exhibit enhanced antiviral effects (Lifson et al., 1988, Science 241:712–716). Nasci et al. (1989, Proc. Natl. Acad. Sci. U.S.A. 86:7139–7143) observed that benzylated derivatives of CD4 appeared to exert a virostatic effect even on cultures which had already been infected with HIV-1, as indicated by decreased p24 production, cytopathicity and cell-mediated infectivity. Inhibition of HIV-1 induced syncytium formation has been reported by Hayashi et al. (1989, Arch. Virol. 105:129–135), using synthetic peptide fragments comprising amino acid residues 70–132 of CD4, and by Chao et al. (1989, J. Biol. Chem. 264:5812–5817), using a 113 amino acid fragment of CD4.

Other HIV inhibitory peptides currently being studied include peptides which interact with the HIV-1 protease (Bellich et al., 1988, J. Biol. Chem. 263:17905–17908 ). Moore et al. (1989, Biochem. Biophys. Res. Commun. 159:420–425) reported that certain oligopeptides which contain a consensus retroviral protease cleavage site, when certain key amino acid residues are altered, may serve as HIV-1 protease inhibitors.

Alternatively, peptides derived from membrane associated viral proteins have been investigated. Moore et al. (1988, Immunopharmacol. 16:181–189) reports in vivo depression of lymphocyte traffic in sheep by an HIV gp120 related peptide.

HIV transmembrane protein gp41 has been associated with immunosuppression. Cauda et al. (1988, Cell Immunol. 115:57–65) reports that natural killer cell activity appeared to be inhibited by synthetic peptides corresponding to amino acid residues 735–752 and 846–860 of HTLV-IIIB gp160, corresponding to regions in gp41. Ruegg et al. (1989, J. Virol. 63:3257–3260) observed that a peptide consisting of amino acids 581–597 of gp41 (see FIG. 1) specifically inhibited human and murine lymphoproliferation; similarly, Chanh et al. (1988, Cell Immunol. 111:77–86) reports that synthetic peptides corresponding to amino acids 735–752 and 846–860 of HTLV-IIIB gp160 suppressed the normal human lymphocyte blastogenic response. Cianciolo et al. (1988, Immunol. Lett. 19:7–13) observed that synthetic peptides corresponding to a conserved sequence within transmembrane envelope proteins of HTLV-1 (CS-1) and HIV (CS-3, derived from gp41 and having the amino acid sequences LQARILAVERYLKDQQL) are capable of suppressing the in vitro proliferative response of human T lymphocytes to mitogenic or allogeneic stimuli, and further noted that the effect appeared to be T-cell specific in that B cell proliferation in response to anti-IgG was not altered by CS-3, European Patent Application, EP 88312216 by Kemp et al., filed December 12, 1988, and claiming priority to Australian patent applications AU 876101 (filed Dec. 12, 1987) and AU 8827573 (filed Dec. 23, 1988), relate to peptides derived from gp41 in methods for treatment or prophylaxis of HIV infections, contending that these peptides disrupt the interaction between gp41 and gp120 envelope proteins of HIV particles.

Antibodies directed toward viral peptides are also being considered as therapeutic options. Rusche et al. (1988, Proc. Natl. Acad. Sci. U.S.A. 85:3198–3202) relates to antibodies which bind to a 24 amino acid sequence of gp120 and thereby inhibit fusion of HIV-infected cells. Dalgleish et al. (1988, Virology 165:209–215) reports that three monoclonal antibodies raised against synthetic peptide analogous to a hydrophilic region of gp41 neutralize different HIV-1 isolates but not HIV-2 isolates. Alternatively, anti-idotype antibodies, directed toward anti-CD4 antibodies, have been shown to bind to HIV virus in vitro, presumably by possessing protein configurations similar to CD4 determinants (Dalgleish et al., 1989, UCLA Symposia on Molecular and Cellular Biology, J. Cell Biochem. Supp. 13B, p. 298).

3. SUMMARY OF THE INVENTION

The present invention relates to methods of inhibiting HIV-mediated cell killing and infection which comprises inhibiting the interaction between the CS3 region of viral gp41 and its cellular receptor. In particular, the invention relates to the discovery that a 17 amino acid region of HIV transmembrane glycoprotein gp41(TM), comprising amino acids 583–599 and denoted as CS3, binds to a unique cellular receptor. The invention provides for methods which employ peptides, peptide derivatives, or antibodies to inhibit the CS3/CS3 receptor interaction. In addition, the invention also relates to the CS3 receptor, which may be required for high affinity binding of HIV to cells. According to the invention, the CS3 receptor or portions or derivatives thereof, or antibodies directed toward the receptor, may be used to inhibit the virus/CS3 receptor interaction. As the CS3 receptor has been identified on the surface of neuroblastoma cells methods of blocking the CS3 receptor/HIV interaction may be used in the treatment of HIV-associated nervous system disorders.

The present invention also provides for an assay system to detect and/or quantitate HIV binding to cells. The present invention is based in part on the discovery that a CS3 specific cellular receptor is widely distributed on human lymphocytes and forms a 108 kd complex with CS3-HSA peptide conjugate. It was further discovered that CS3 peptide effectively blocks HIV binding, infection, and virus-mediated cell killing. Therefore, the present invention provides for methods of treatment and prophylaxis of HIV infection as well as a means for better understanding the physiology of acquired immunodeficiency syndrome (AIDS).

3.1. Abbreviations

FITC—fluoroscein isothiocyanate

HIV—human immunodeficiency virus

HSA—human serum albumin

4. DESCRIPTION OF THE FIGURES

FIG. 1. Nucleic Acid and Amino Acid Sequences of the env gene in five independent HIV isolates (Starcich et al., 1986, Cell 45:637–648) gp41.

FIG. 2. Flow cytometric analysis of interaction of cys-CS 3-HSA with RH9 cells (A) HSA (EDC-treated) FITC control; (B) CS3-HSA-FITC 4 μg/$10^6$ cells; (C, D, & E) CS3-HSA-FITC in the presence of 5×CS3-HSA, 20×CS3-HSA or 50×DC7-HSA (DC7 [ASFDEREPYAH] coupled to HSA at similar ratios of peptide to HSA [11/1] respectively, as competing agents.

Figure 3:
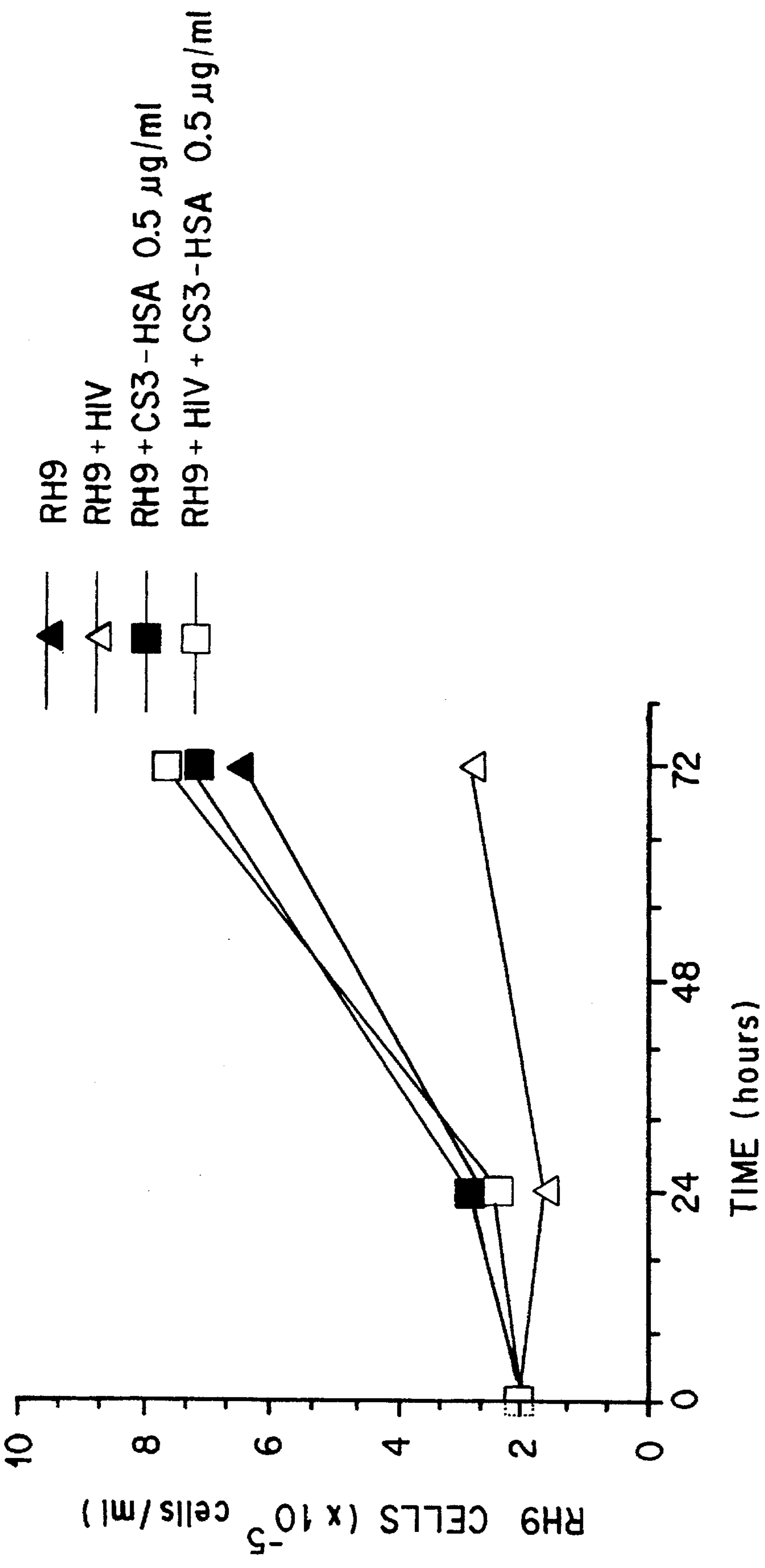

FIG. 3. Effect of CS3-HSA on HIV-mediated cytopathicity of RH9 cells.

Figure 4:
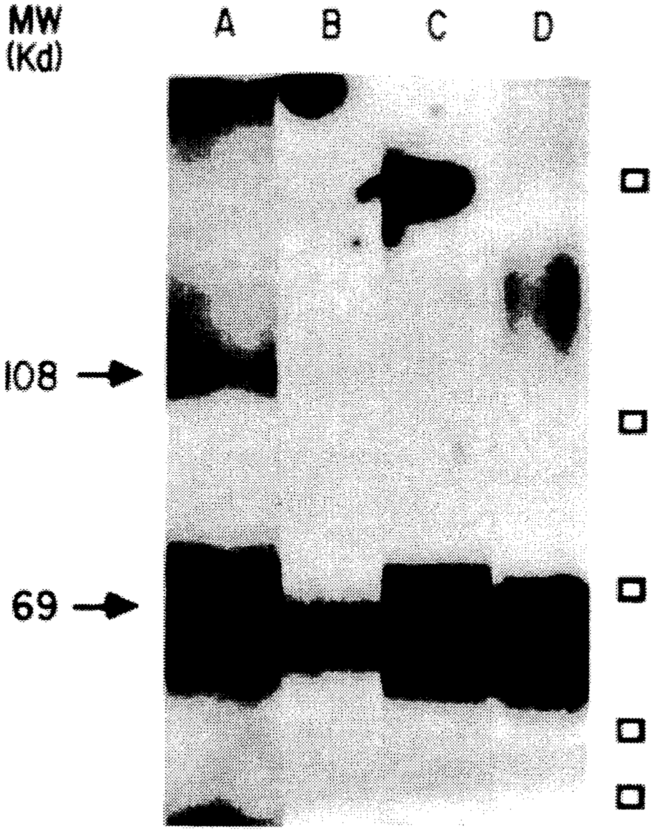

FIG. 4. Cross-linking of radiolabeled CS3-HSA to the CS3 receptor on uninfected RH9 cells (B) with or (A) without 100×cold CS3-HSA as competing agent, and with (A, B, and D) or without (C) the crosslinking agent disuccinimidyl suberate. Irrelevant peptide $I^{125}$-DC7 was used in (D).

Figure 5:
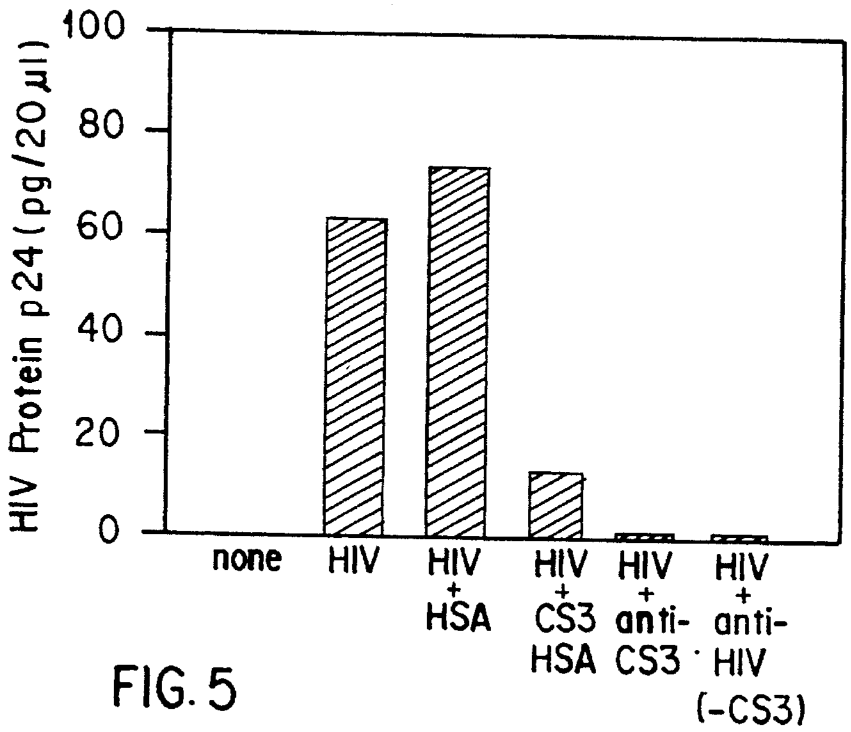

FIG. 5. HIV protein p24 produced in RH9 cells exposed to (i) medium alone ("none"); (ii) HIV alone ("HIV"); (iii) HIV virus and 20 μg/ml HSA ("HIV+HSA"); (iv) HIV virus and CS3-HSA at 10 μg/ml ("HIV+CS3-HSA"); (v) HIV virus and 6.7 μg/ml antibody specific for CS3 ("HIV+anti-CS 3"); or (vi) HIV virus and 6.7 μg/ml CS3 depleted anti-HIV IgG ("HIV+anti-HIV (-CS3)").

Figure 6:
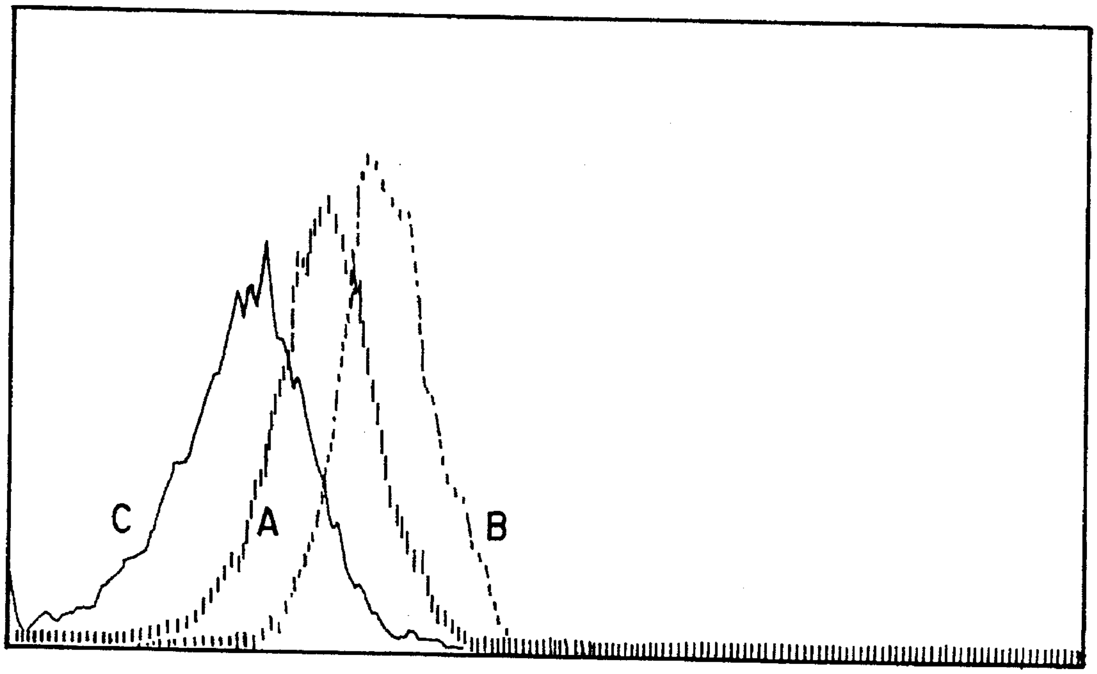

FIG. 6. HIV virus bound to MOLT cells in the presence (A) or absence (B) of CS3-HSA as demonstrated by FACS analysis using CS-3 depleted anti-HIV IgG and FITC-labelled $F(ab)_2$ goat anti-human antibody (fluorescence vs. cell number). (C) represents control cells, exposed to neither virus nor peptide.

Figure 7:
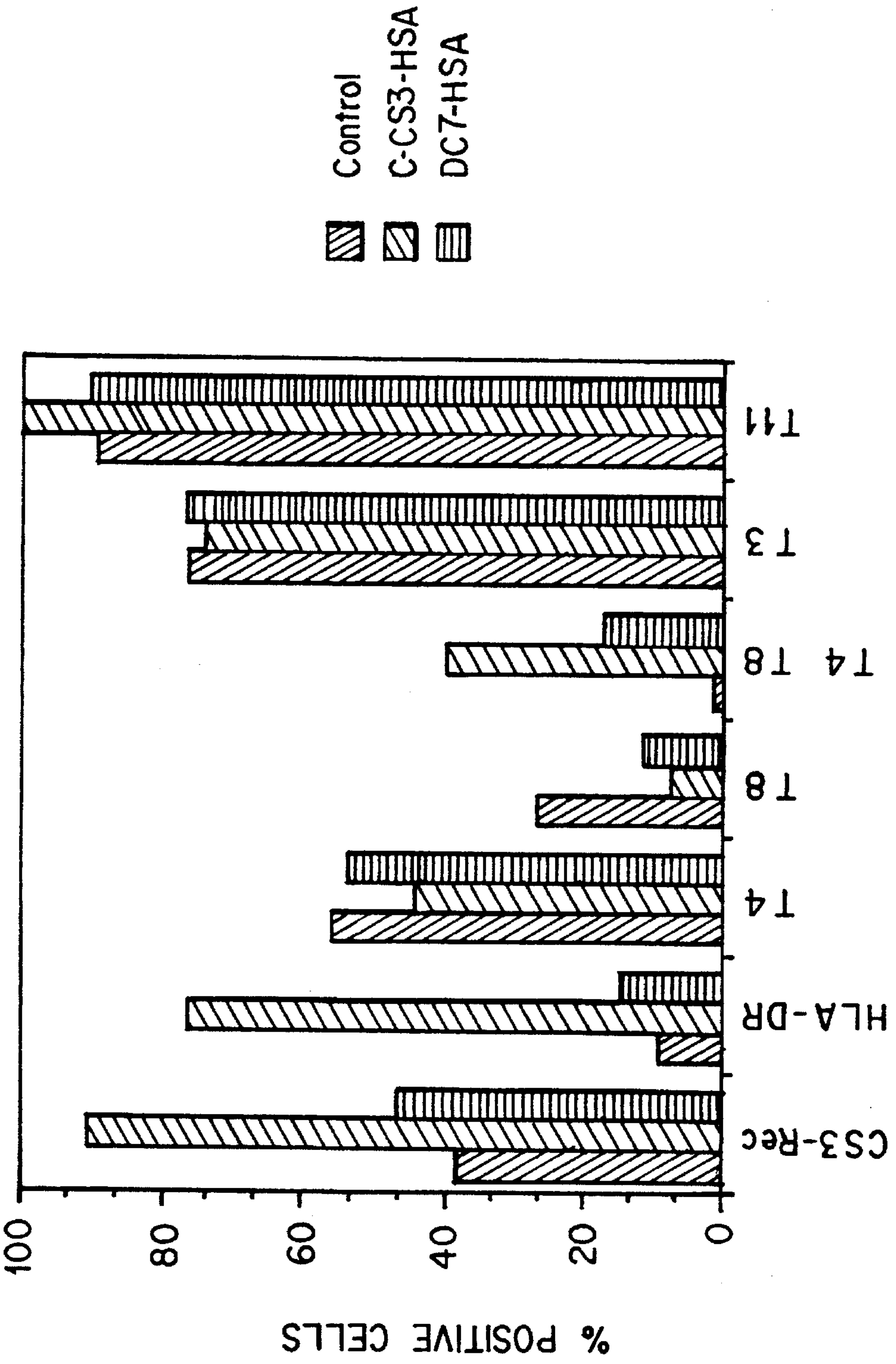

FIG. 7. Expression of CS3 receptor, HLA-DR, T4, T8, T3, and T11 on control cells, and cells treated with c-CS3-HSA or the irrelevant peptide DC7-HSA, as measured by fluorescence flow cytometry.

Figure 8A:
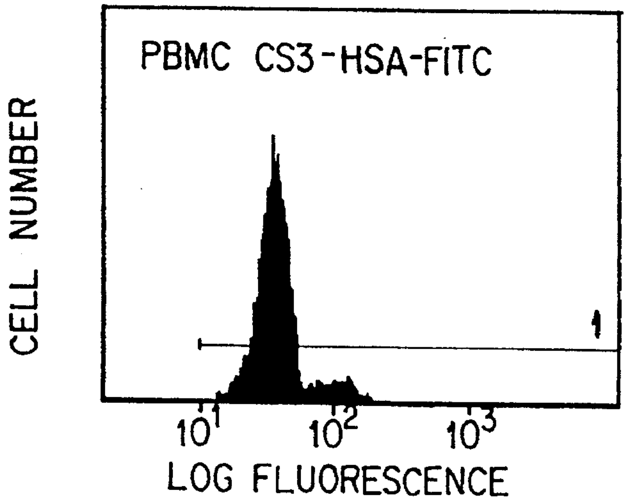
Figure 8B:
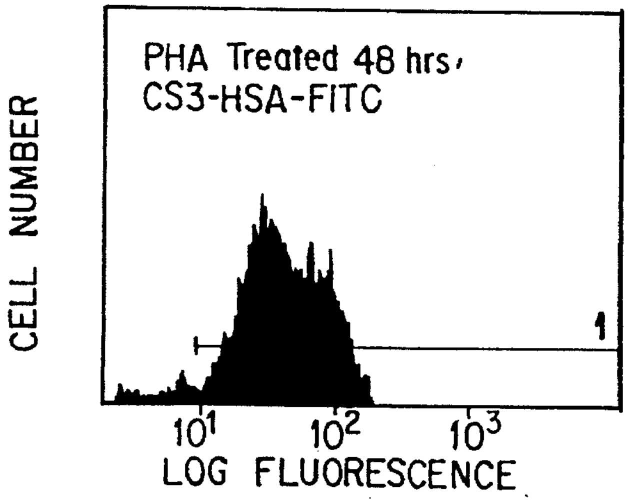
Figure 8C:
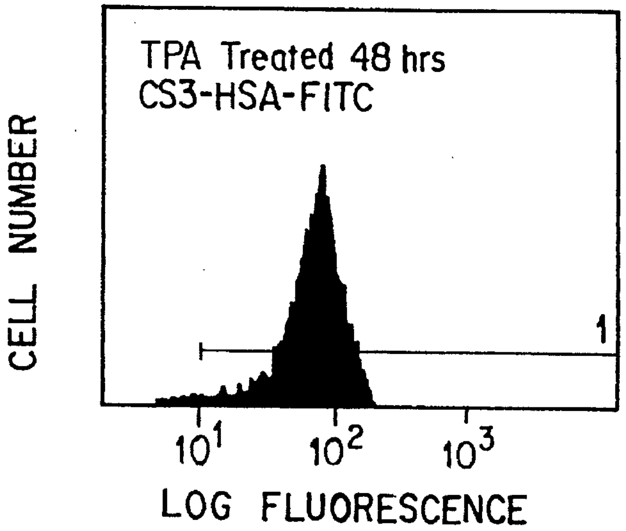

FIG. 8. PBMC were analyzed for cell surface expression of CS3 receptor using CS3-HSA-FITC, either initially or after 48 hours in culture medium without activation (Top panel). Alternatively, PBMC were stimulated with PHA (1 ng/ml) or TPA (a mitogenic phorbol ester, 10 ng/ml) or cultured in medium without mitogen for 48 hours before harvesting and analyzing for expression of CS3 receptor. Comparison of PBMC fresh or cultured without mitogen for 48 hours revealed little difference in the expression of CS3 receptor.

Figure 9:
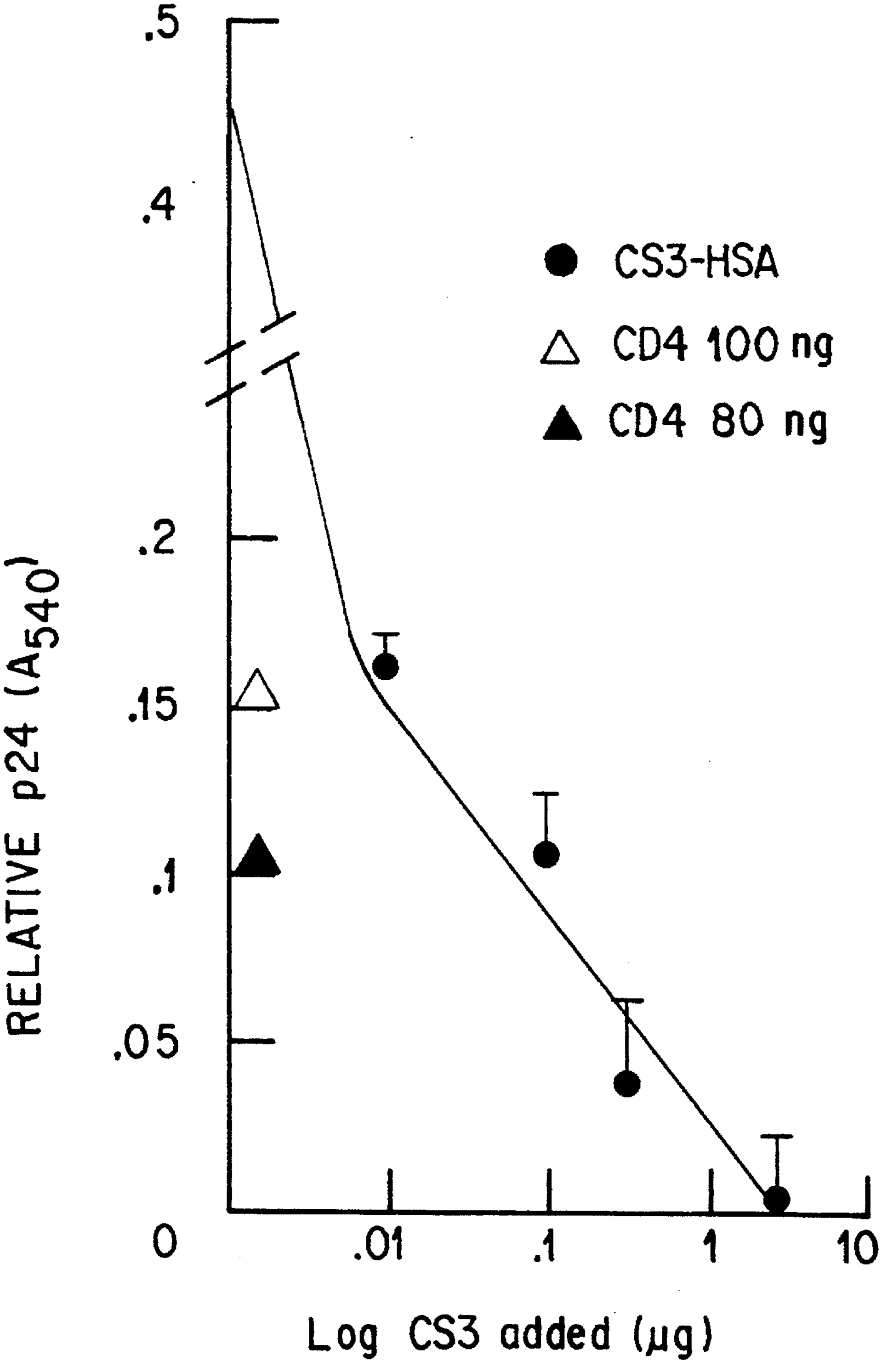
Figure 10A:
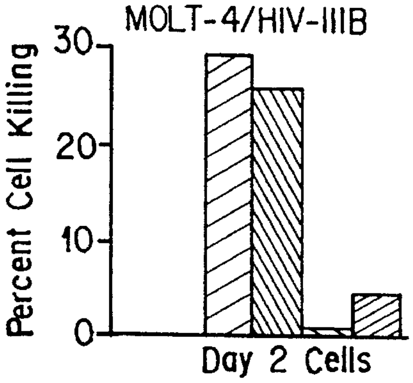
Figure 10B:
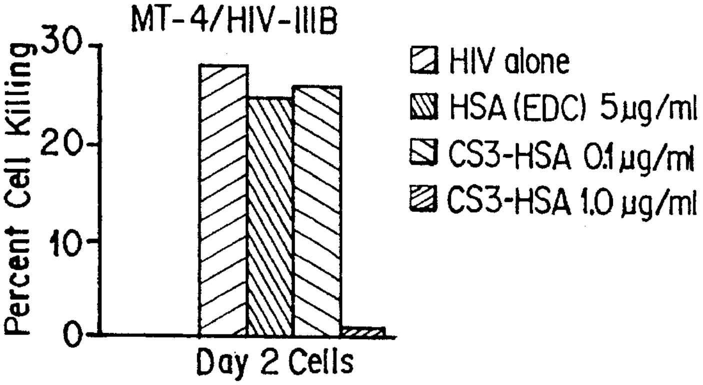
Figure 10C:
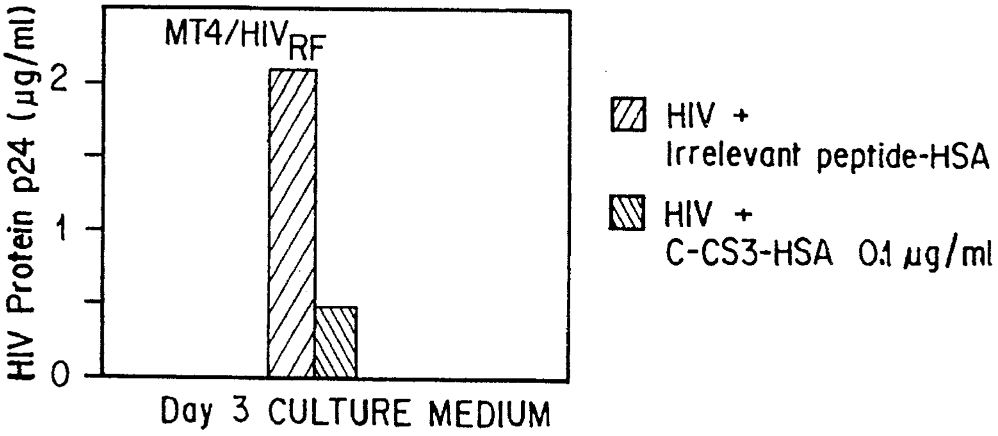
Figure 10D:
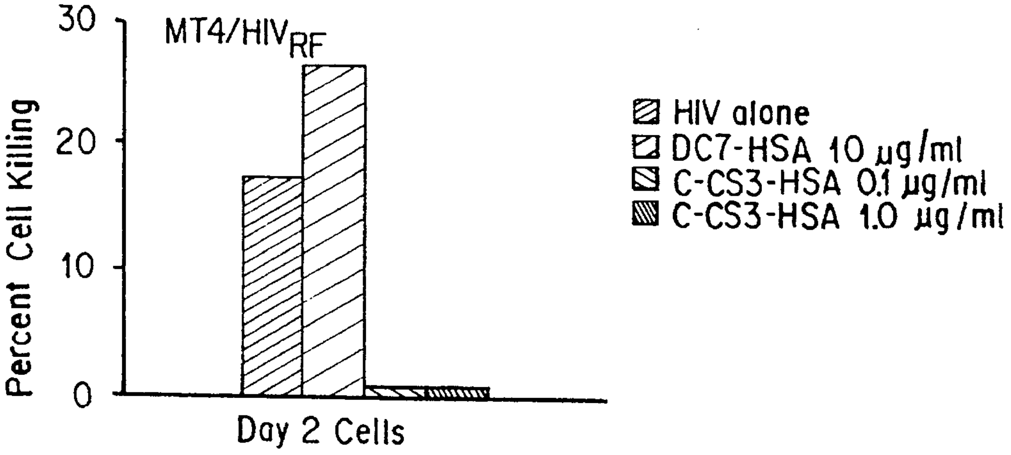
Figure 11B:
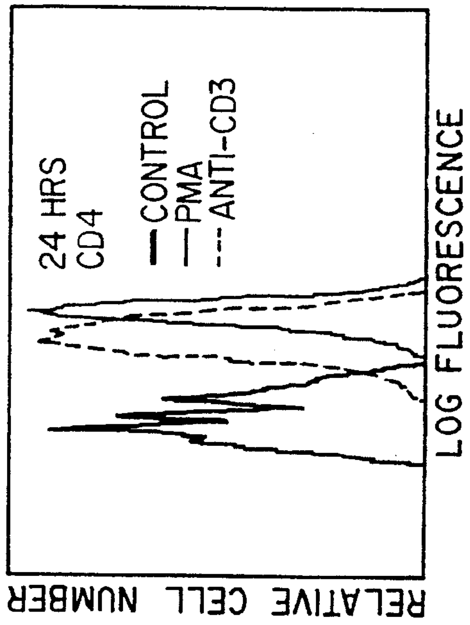
Figure 11D:
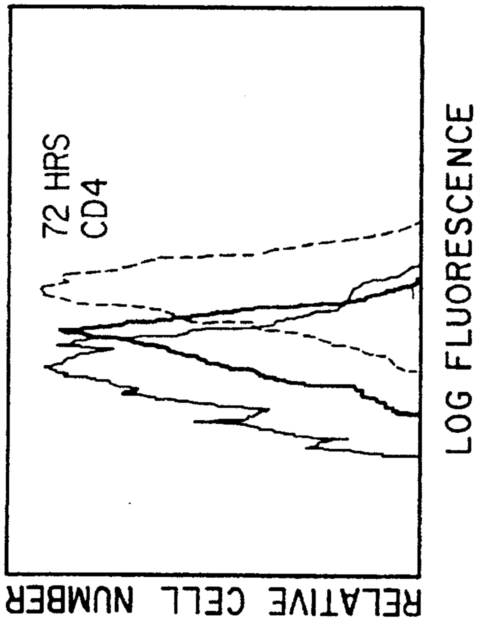
Figure 11A:
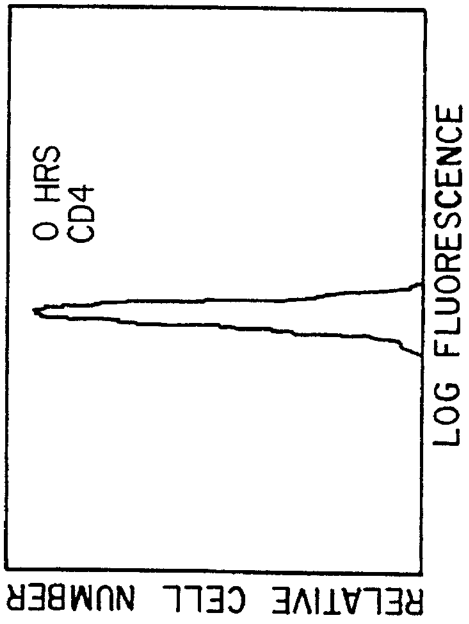
Figure 11C:
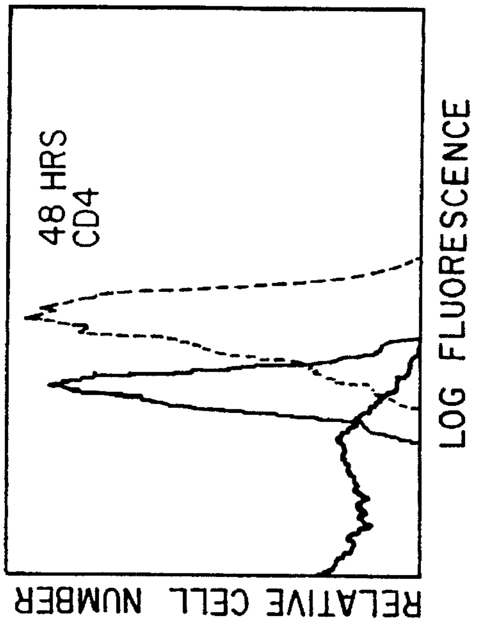
Figure 11E:
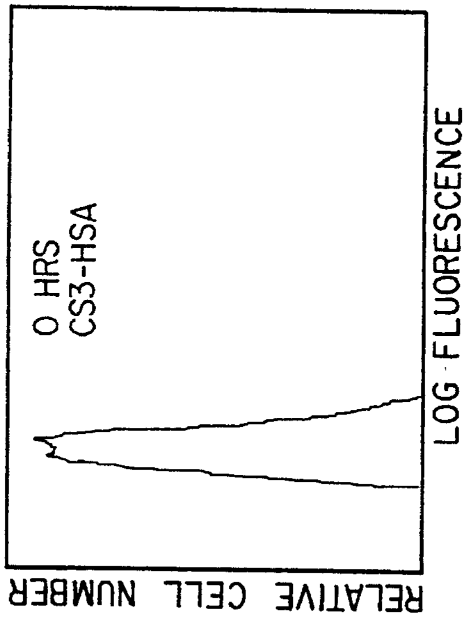
Figure 11F:
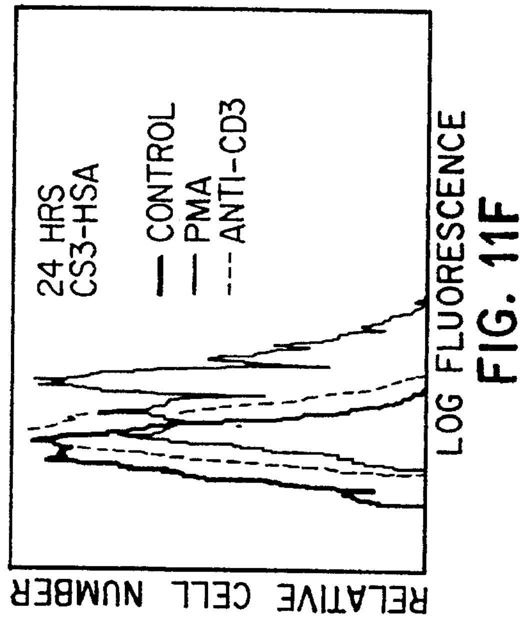
Figure 11G:
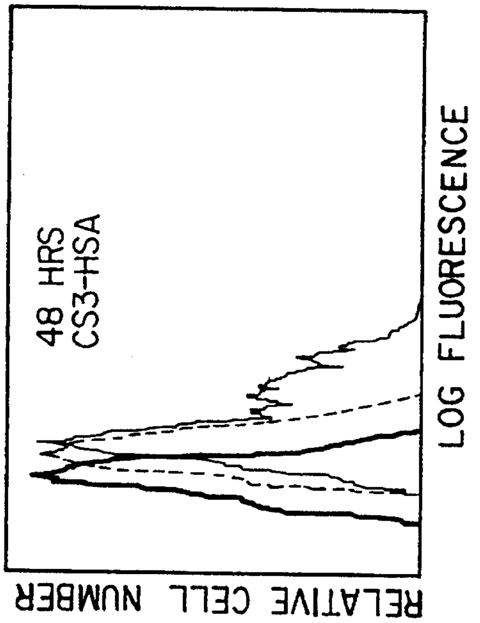
Figure 11H:
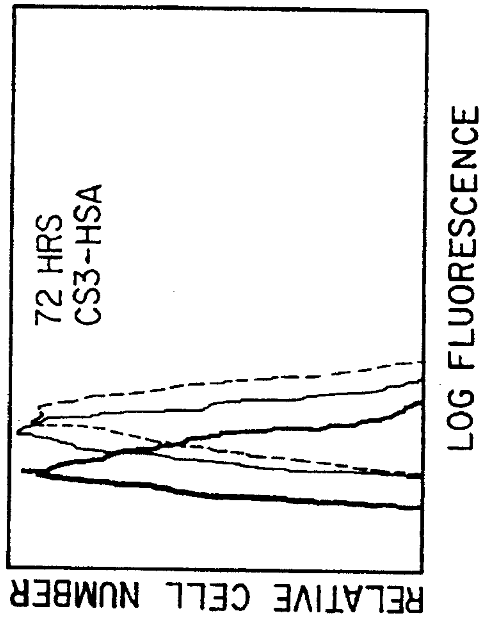

FIG. 9. Inhibition of HIV binding to CD4 cells by sCD4 and CS3-HSA. sCD4 was added to aliquots of HIV, in 100 μl, for 30 minutes on ice prior to addition of $10^6$ MT4 cells for an additional 30 minutes on ice. CS3-HSA was added to cells for 30 minutes on ice prior to addition of HIV for an additional 30 minutes. Following this the incubations were layered over 6:1 mixture of silicon oil to fluid. Following microfuge centrifugation for 30 seconds the tube was frozen in liquid $N_2$. The cell pellet was snipped off and solubilized for the Abbott antigen capture assay.

FIG. 10. A. Killing of MOLT4 cells by $HIV_{IIIB}$. B. Killing of MT4 cells by $HIV_{rf}$. C. Protection of MT4 from $HIV_{rf}$ infection. Effect of CS3-HSA on HIV mediated cytopathicity. Cells at $2\times10^5$ cells/ml in RPMI medium containing 10% FCS were treated as indicated for 4 hours with peptide conjugates and/or HIV. The cells were then washed twice in 10× volume of HBSS and resuspended to the original volume in 25 $cm^2$ flasks. Number of viable cells were determined by trypan blue exclusion. HIV stocks were prepared by 100,000×g centrifugation of culture supernatants from chronically infected RH9 cells. Resuspended pellets were aliquoted and stored at –70° C. Results represent an average of duplicate flasks from which four fields were counted on a hemocytometer. The number of cells in duplicate flasks varied by less than 5%. To assess HIV infection quantitative analysis for p24 was performed using the FDA approved assay by Abbott Laboratories.

FIG. 11. Cultures of RH9 cells were incubated with 10 ng/ml PMA (TPA) or 10 μg/ml antibody to the CD3 cell surface antigen or in medium alone. Comparisons are presented for each day of analysis for expression of CD4 (left panel) or CS3 binding (right panel). 0.50% of RH9 cells bound CS3-HSA-FITC. Relative to control cultures treatment with anti-CD3 increased CS3 domain expressing cells by 71% at 48 hours and 56% at 72 hours, while TPA increased CS3-binding by 32% at 72 hours. CS3-HSA-FITC fluorescence intensity, reflecting the number of receptors per cell, increased while CD4 expression decreased in intensity and number of positive cells (8% at 24 hours).

Figure 12:
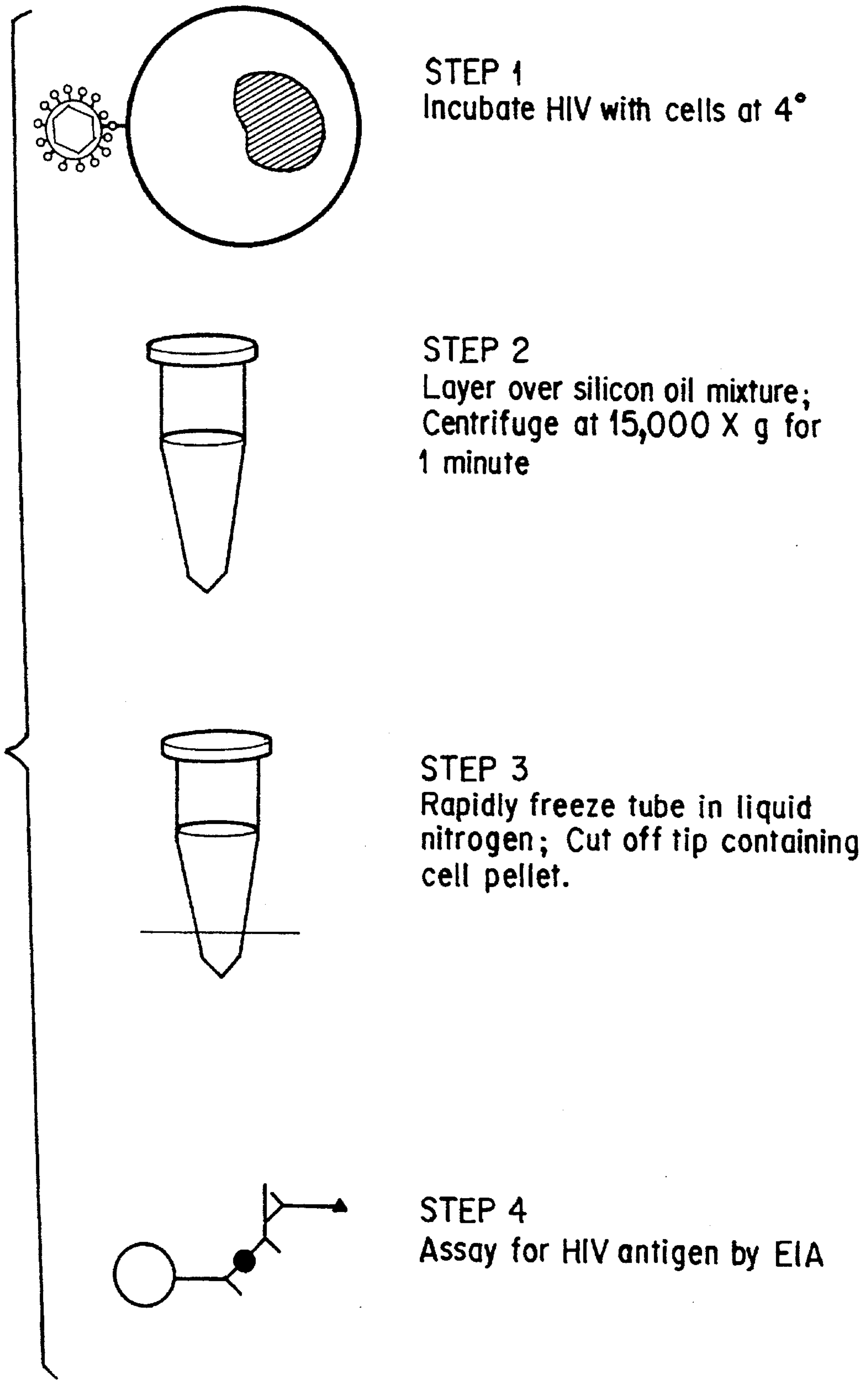

FIG. 12. Schematic diagram of HIV cell binding assay.

Figure 13:
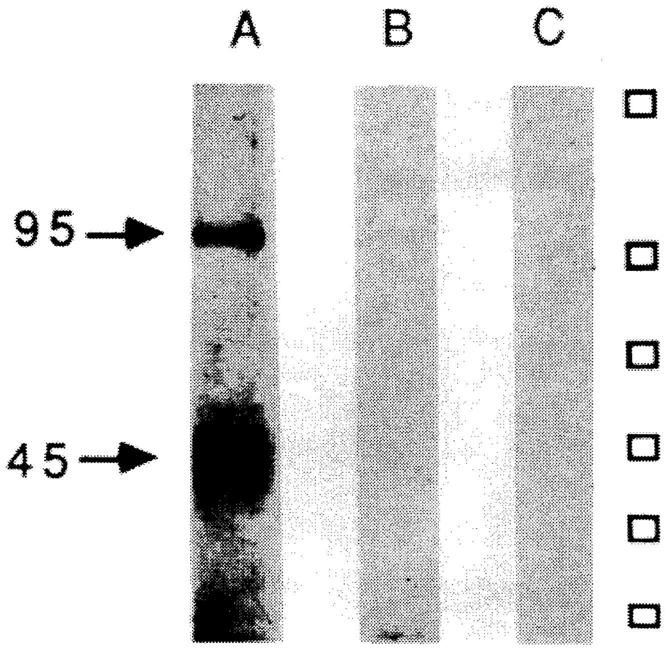

FIG. 13. Crosslinking of 125-I-CCS3-APG to cell surface receptor polypeptides. 125-I-CCS3 was incubated with 6 mM azidophenylglyoxal in the dark for one hour. RH9 cell pellets of $10^6$ cells each were incubated with a 100× concentration of CCS3, CCS3-HSA or medium (RPMI 1640, 1% FCS) for 30 minutes on ice prior to addition of 125-I-CCS3-APG (1 μg) for an additional 30 minutes incubation on ice. The cells were washed twice with PBS then resuspended in 0.5 ml PBS and exposed to UV light for 30 minutes (uv light box, FotoDyne). The cells were pelleted, then resuspended in solubilization buffer (PBS, 0.1% triton X-100, 1 mM PMSF), vortexed, then microfuged at 10,000×g for 10 minutes. The lysate was diluted with an equal volume of 2× sample buffer with or without 2-mercaptoethanol then run on a 7% SDS PAGE. Lane A is 125-I-CCS3-APG alone; B, preincubation with 100 μg CCS3; C, preincubation with 100 μg CCS-HSA. Molecular weight markers are, from top to bottom, myosin at 200 kd, phosphorylase b at 92.5 kd, bovine serum albumin at 69 kd, ovalbumin at 46 kd, carbonic anhydrase at 30 kd, and trypsin inhibitor at 21.5 kd.

5. DETAILED DESCRIPTION OF THE INVENTION

The present invention relates to methods of inhibiting HIV-mediated cell killing and infection which comprise inhibiting the interaction between the CS3 region of viral gp41 and a novel cellular receptor. For purposes of clarity of disclosure, and not by way of limitation, the description of the present invention will be divided into the following subsections:

(i) peptides of the invention
(ii) antibodies of the invention
(iii) utility of the invention

5.1. Peptides of the Invention

Any peptide or protein which inhibits the interaction between the CS3 region of viral gp41 (or its homologue in other retroviruses, including those which infect human as well as nonhuman hosts) may be used according to the invention. In various embodiments of the invention, these inhibitors may include peptides related to the CS3 region of gp41, or derivatives thereof, as well as peptides or proteins which are identical or homologous to the CS3 receptor, or portions thereof. Antibodies may also be used, and are discussed in section 5.2, infra.

Peptides related to the CS3 region of gp41 are, according to the invention, identical or homologous to the amino acid sequence LQARILAVERYLKDQQL, or a portion thereof or, alternatively, to a homologous peptide sequence associated with another virus, including, but not limited to, HIV-2, in which the corresponding amino acid sequence is substantially LQARVTAIEKYLQDQA. Peptides related to the CS3 region may comprise at least three sequential residues of LQARILAVERYLKDQQL, or a homologous peptide, but preferably comprise at least 8 residues, and most preferably all 17 residues of this sequence. The term CS3-related peptides should be construed to mean peptides in which amino acids are substituted by functionally equivalent amino acids (see infra) as well as derivatives of these peptides, including but not limited to benzylated derivatives, glycosylated derivatives, and peptides which include enantiomers of naturally occurring amino acids. In the preferred embodiments of the invention, the CS3 peptides, related peptides or derivatives are linked to a carrier molecule such as a protein, including but not limited to, HSA. CS-3 related peptides comprising additional amino acids may also be used according to the invention. In a preferred embodiment of the invention, a cysteine residue may be added to the N-terminal portion of the peptide. It has been observed that Cys-CS3-HSA binds to the CS3 receptor with higher affinity.

Peptides may be produced from naturally occurring or recombinant viral proteins, or may be produced using standard recombinant DNA techniques (e.g. the expression of peptide by a microorganism which contains recombinant nucleic acid molecule encoding the desired peptide, under the control of a suitable transcriptional promoter, and the harvesting of desired peptide from said microorganism). Preferably, the peptides of the invention may be synthesized using any methodology known in the art, including but not limited to Merrifield solid phase synthesis (Clark-Lewis et al., 1986, Science 231:134–139).

Alternatively, peptides or proteins which are identical or homologous to the CS3 receptor may be utilized according to the invention. The CS3 receptor may be isolated and characterized using any method known in the art based on the discovery of the present invention that the CS3 region of gp41 binds to a specific cellular receptor. For example, and not by way of limitation, CS3 receptor may be isolated from extracts of lymphocyte cell membranes either by affinity chromatography, in which CS3 peptide is bound to a solid support, or by preparative SDS-polyacrylamide gel electrophoresis, in which gel slices containing the CS3 receptor are identified by allowing labeled CS3 peptide to bind to the receptor. As described in section 8, infra, the CS3 receptor forms a complex with $^{125}I$ labelled CS3-HSA that has an apparent molecular weight of 108 kd. In preferred embodiments of the invention, CS3 receptor may be freed from cross-linked peptide, or may be separated from other proteins by polyacrylamide gel electrophoresis and then identified by subsequent binding to labelled CS3. CS3 may require further purification before it may either be used according to the methods of the invention, or, preferably, be subjected to amino acid sequencing (e.g. Hewick, 1981, J. Biol. Chem. 256:7990–7997 ). Oligonucleotide probes corresponding to amino acid sequence thus obtained may then be generated by standard techniques, and then used to identify cDNA or genomic clones encoding the CS3 receptor using standard techniques including polymerase chain reaction (Saiki et al., 1985, Science 230:1350–1354). Once the CS3 receptor gene has been cloned, CS3 receptor may then be produced in quantity using standard expression systems, including, but not limited to, vaccinia virus and baculovirus expression vector systems. Alternatively, anti-CS3 receptor antibody may be generated as described below and then used to clone the CS3 receptor gene by polysome precipitation. In a preferred embodiment of the invention, the CS3 receptor gene may be cloned by a "shotgun" approach in which genomic DNA or, preferably, lymphocyte cDNA may be used to create an expression library in which clones expressing the CS3 receptor may be identified by binding to labelled CS3-HSA. CS3 receptor, or derivatives or portions thereof, may be utilized according to the invention.

The present invention also provides for a CS3 receptor which comprises two polypeptide subunits, in which one subunit has a molecular weight of between about 43 and 47 kd and the other has a molecular weight of between about 93 and 97 kd. The present invention provides for each of these subunit peptides.

Useful CS3 related peptides and useful portions or derivatives of the CS3 receptor may be preferably identified using an assay system which can detect inhibition of the CS3 peptide/CS3 cellular receptor interaction. For example, and not by limitation, potentially useful CS3 related peptides and CS3 receptor related peptides may be tested for their ability to block HIV mediated cytopathicity of RH9 cells as described in Section 7, infra. Alternatively, CS3 peptides may be tested for their ability to block HIV binding to cells.

The CS3 peptides or proteins, or fragments or derivatives thereof, of the invention include, but are not limited to, those containing, as a primary amino acid sequence, all or part of the amino acid sequence LQARILAVERYLKDQQL (or a homologous peptide, for example, the homologous peptide from HIV-2) including altered sequences in which functionally equivalent amino acid residues are substituted for residues within the sequence resulting in a silent change. For example, one or more amino acid residues within the sequence can be substituted by another amino acid of a similar polarity which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

Because it appears that CS3 peptide is capable of partially activating lymphocytes (see Section 11, infra), and upregulates expression of its own receptor, it may be useful to utilize CS3 related peptides which are not associated with partial lymphocyte action but which continue to block the virus/CS3 receptor interaction. For example, and not by way of limitation, such peptides may comprise D-amino acids, or may comprise an inefficient carrier protein, or no carrier protein at all. It has been observed that CS3 unconjugated to HSA fails to partially activate lymphocytes.

Also included within the scope of the invention are CS3 and CS3 receptor proteins or fragments or derivatives thereof which are differentially modified during or after translation, e.g., by glycosylation, proteolytic cleavage, linkage to an antibody molecule or other cellular ligand, etc.

5.2. Antibodies of the Invention

The present invention also relates to antibodies which inhibit the interaction between CS3 and its cellular receptor. Such antibodies may be directed toward, for example, epitopes in or near the CS3 peptide region of gp41, or in or near the binding site of the CS3 peptide region on the CS3 receptor.

The antibodies may be produced using, as immunogen, all or portions of gp41, the CS3 peptide region (LQARILAVERYLKDQQL or a homologous peptide), or the CS3 receptor. Alternatively, antiidiotype antibodies directed toward antibodies which interact with gp41, the CS3 peptide, or the CS3 receptor, may be inhibitory to the CS3 peptide region/CS3 receptor interaction.

For preparation of monoclonal antibodies directed toward CS3 or gp41 or the CS3 receptor any technique which provides for the production of antibody molecules by continuous cell lines in culture may be used. For example, the hybridoma technique originally developed by Kohler and Milstein (1975, Nature 256:495–497), as well as the trioma technique, the human B-cell hybridoma technique (Kozbor et al., 1983, Immunology Today 4:72), a method such as that described in Huse et al., 1989, (Science 246:1275–1281) and the EBV-hybridoma technique to produce human monoclonal antibodies (Cole et al., 1985, in "Monoclonal Antibodies and Cancer Therapy," Alan R. Liss, Inc. pp 77–96) and the like are within the scope of the present invention.

The monoclonal antibodies for therapeutic use may be human monoclonal antibodies or chimeric human-mouse (or other species) monoclonal antibodies. Human monoclonal antibodies may be made by any of numerous techniques known in the art (e.g., Teng et al., 1983, Proc. Natl. Acad. Sci. U.S.A. 80:7308–7312; Kozbor et al., 1983, Immunology Today 4:72–79; Olsson et al., 1982, Meth. Enzymol. 92:3–16). Chimeric antibody molecules may be prepared containing a mouse antigen-binding domain with human constant regions (Morrison et al., 1984, Proc. Natl. Acad. Sci. U.S.A. 81:6851, Takeda et al., 1985, Nature 314:452).

Various procedures known in the art may be used for the production of polyclonal antibodies to epitopes of gp41, CS3, or CS3 receptor. For the production of antibody, various host animals can be immunized by injection with the immunogenic protein, or fragment or derivative thereof, including, but not limited to, rabbits, mice, rats, etc. Various adjuvants may be used to increase the immunological response, depending on the host species, and including, but not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum.*

A molecular clone of an antibody to a gp41, CS3 or CS3 receptor epitope can be prepared by known techniques. Recombinant DNA methodology (see e.g., Maniatis et al., 1982, Molecular Cloning, A Laboratory Manual, Cold Spring Harbor Laboratory, Cold Spring Harbor, N.Y.) may be used to construct nucleic acid sequences which encode a monoclonal antibody molecule, or antigen binding region thereof.

Antibody molecules may be purified by known techniques, e.g., immunoabsorption or immunoaffinity chromatography, chromatographic methods such as HPLC (high performance liquid chromatography), or a combination thereof, etc.

Antibody fragments which contain the idiotype of the molecule can be generated by known techniques. For example, such fragments include, but are not limited to: the $F(ab')_2$ fragment which can be produced by pepsin digestion of the antibody molecule; the Fab' fragments which can be generated by reducing the disulfide bridges of the $F(ab')_2$ fragment, and the 2 Fab or Fab fragments which can be generated by treating the antibody molecule with papain and a reducing agent.

5.3. Utility of the Invention

The CS3 related peptides, CS3 receptor proteins or peptides, or antibodies of the invention may be utilized to inhibit retrovirus mediated cell killing and may, accordingly, be used in the treatment of HIV infection and also in prophylaxis against HIV infection. The peptides or antibodies of the invention may be administered to patients in any sterile biocompatible pharmaceutical carrier, including, but not limited to, saline, buffered saline, dextrose, and water. Methods of introduction include, but are not limited to, intradermal, intramuscular, intraperitoneal, intravenous, subcutaneous, oral, and intranasal. In addition, it may be desirable to introduce the pharmaceutical compositions of the invention into the central nervous system by any suitable route, including intraventricular and intrathecal injection.

The invention also provides for pharmaceutical compositions comprising CS3 related or CS3 receptor peptides, peptide fragments, or derivatives administered via liposomes, microparticles, or microcapsules. In various embodiments of the invention, it may be useful to utilize such compositions to achieve sustained release of CS3 related peptides or CS3 receptor peptides.

An exemplified in Section 7, infra, CS3 related peptides, have been found to inhibit HIV binding and HIV-mediated lymphocyte infection and killing. In a specified embodiment of the invention, CS3-HSA may be used to inhibit HIV-mediated cell killing in a person or animal in need of such treatment. CS3 may also be linked to another suitable molecular carrier other than HSA, or may be administered free of carrier. By blocking the cellular receptor for virus, infection of the target cells may be prevented.

Similarly, the CS3 receptor, or portions or derivatives thereof relevant to the virus-CS3 receptor interaction, may be used as decoys for viral attachment. The CS3 receptor, portions or derivatives thereof may be administered to a person or animal in need of such treatment. It may be desirable to administer the CS3 receptor, or peptides or derivatives thereof, linked to a molecular carrier, for example, but not limited to, HSA. Likewise, the antibodies of the invention, directed toward CS3 or its receptor, may be administered to persons or animals in need of such treatment.

The CS3 peptides, CS3 receptor, or antibodies may be administered to subjects who suffer from retroviral infection (e.g. acquired immunodeficiency syndrome or AIDS-related complex (ARC)) as well as to those at risk for retroviral infection.

As the CS3 receptor has been identified on the surface of neuroblastoma cells methods of blocking the CS3 receptor/HIV interaction may be used in the treatment of HIV-associated nervous system disorders.

The CS3 peptides, CS3 receptor, and antibodies of the invention may also be used to study the mechanisms of retroviral infection and, additionally, lymphocyte activation. Defining the tissue distribution of the CS3 receptor may also be useful in identifying portals for virus entry in non-lymphocyte tissues. As shown in Example Section 12, a variety of cell lines have been observed to express the CS3 receptor indicating that the CS3 receptor may be expressed in multiple tissue types and human and nonhuman species. CS3 receptor has been observed on macrophages. The CS3 receptor may be the entrance for HIV into the central nervous system, via macrophages or via neurons themselves.

The present invention also provides for an assay system to measure or detect HIV binding as exemplified in Section 13, infra. A binding assay has been developed for viruses, particularly HIV, which has broad application for screening for antivirals (drugs, peptides and antibodies) that are potentially neutralizing by virtue of the ability to prevent binding of virus to target cells (See FIG. 13). The binding assay comprises exposing cells to virus (e.g. HIV) in medium for a period of time sufficient to allow binding of virus to cells to occur, centrifuging the cells and virus through a high specific gravity liquid such as, preferably, silicon oil, freezing the media and cell pellet, separating the cell pellet from the frozen medium, and assaying the cell pellet for viral core protein. This assay may be used to test the ability of a compound (e.g. a peptide) to block virus biding. For example, CS3-HSA may be incubated with MT4 cells prior to the addition of HIV (5–6 infectious particles per cell). Cells may then be centrifuged (preferably microfuged) through silicon oil, the tube may then be frozen (for example in liquid $N_2$) then the pellet snipped off to separate it from the frozen medium. The cell pellet may then be assayed for p24 core antigen content using, for example, the Abbott assay or any suitable HIV assay system known in the art. For its use with HIV, freezing the tube is essential to prevent any HIV from the medium from contaminating the cell pellet. Analysis of core protein is also an important feature, since gp120 from particles that do not infect would result in high backgrounds if antibody to gp120 was used. This assay may be used to identify compounds which block HIV/cell binding such as compounds which block HIV binding to the CS3 receptor.

6. EXAMPLE: EXPRESSION OF CS3 RECEPTORS ON LYMPHOCYTES

6.1. Materials and Methods

Cysteine-CS3 (C-CS3, which has the sequence CLQARILAVERYLKDQQL) was coupled to human serum albumin as described (Ciancialo et al., 1988, Immunology Letters 19:7). A molar ratio of 10 CS3/HSA was achieved as determined by addition of trace amounts of $^{125}$I-CS3 to the coupling reaction. C-CS3-HSA was labelled with FITC (Harlow, 1988, in "Antibodies: A Laboratory Manual," Cold Spring Harbor Laboratories, pp. 354–355) and its binding to RH9 cells was determined with the use of Coulter Epics 753 Flow Cytometer. RH9 cells were washed with PBS 1% BSA and incubated with C-CS 3-HSA or controls for 30 min. at 4° C. in a final volume of 100 μl. Cells were washed and resuspended at $10^6$ cells/mi.

6.2. Results and Discussion

The ability of C-CS3 (18 residues, 63.7% polar) to bind to cell surfaces of CD4+ cell lines (RH9 and Jurkat) and human peripheral blood mononuclear cells (PBMC) was examined using flow cytometry. FITC labelled C-CS3-conjugated to HSA (C-CS3-HSA-FITC) was found to bind to RH9 cells (FIG. 2), Jurkat cells and normal human peripheral blood T cells, B cells and mononuclear cells. In contrast, an irrelevant peptide conjugate of similar size, DC7-HSA (11 residues, 52.9% polar) did not bind directly to RH9 nor compete with C-CS3-HSA-FITC binding when added at a 50 fold higher concentration. Further, even a 100 fold excess of HSA (carried through the conjugation procedure) failed to effect a decrease in the binding of C-CS3-HSA-FITC. Conversely, C-CS3-HSA was an effective inhibitor for binding of C-CS3-HSA-FITC with a 20-fold excess almost eliminating C-CS3-HSA-FITC binding.

C-CS3-HSA-FITC labelled 98% of RH9 cells at 4 μg/$10^6$ cells and further addition did not increase the fluorescence intensity. C-CS3-HSA-FITC at 1 μg/$10^6$ RH9 showed minimal binding. Jurkat cells and normal human peripheral blood T cells, B cells and mononuclear cells were also positive by flow cytometry. PBMC subset analysis was performed by dual staining with C-CS3-HSA-Rho and fluorescein labelled monoclonal antibodies (Coulter Cytometry) to CD4, CD8, CD2 for T cells (T4, T8 and T11, respectively), HLA-DR for B (I2) and CD11b or CD14 for monocytes (MO1 and MO2, respectively). Analysis revealed 90% of CD2, CD4 or DR cells were CS3 positive, 87% of MO1 or MO2 cells were CS3 positive and 60% of CD8 cells were CS3 positive. Direct conjugation of FITC to CS3 was ineffective in staining, perhaps due to conformational restraints or alteration of critical side chains. Flow cytometric results using CS3-HSA-FITC yielded lower binding on RH9 cells (20–25 %), than with C-CS3-HSA-FITC (98%) at similar concentrations. The reason for this difference is unknown, but may be due to favorable conformational effects caused by an additional N-terminal residue.

Thus, a putative cell surface receptor which is specific for C-CS3 is broadly distributed on human lymphocytes and is represented on CD4$^+$ cell lines. Similar experiments with CS3-HSA yielded lower binding on RH9 cells (20–25%), although as seen below, both are effective in inhibiting HIV mediated killing of RH9 and in cross-linking to receptor. The reason for this difference is unknown, but may be related to the ability of cysteine residues to stabilize peptide binding to receptors. Importantly, cys-CS 3-HSA bound in a saturable manner and was specific as shown by competition assays (FIG. 2).

7. EXAMPLE: INHIBITION OF HIV-MEDIATED CELL KILLING BY CS3-HSA

7.1. Materials and Methods

RH9 cells at $2\times10^5$ cells/ml in RPMI medium containing 10% FCS were treated as indicated for 4 hrs with peptide conjugates and/or HIV. The cells were then washed twice in 10× volume of HBSS and resuspended to the original volume in 25 $cm^2$ flasks. The number of viable cells was determined at the end of 24, 48 and 72 hours by trypan blue exclusion. HIV stocks were prepared by 100,000×g centrifugation of culture supernatants from chronically infected RH9 cells. Resuspended pellets were frozen at −70° C. in aliquots and used at doses in which a tested frozen aliquot essentially eliminated cell growth by day 3. Numerous cell fragments and debris are evident in these cultures as a result of cell killing. Results represent average of duplicate flasks from which 4 fields were counted on a hemacytometer. Difference in cell numbers in duplicate flasks was less than 5%.

7.2. Results and Discussion

The density of the putative receptor for cys-CS3 increased approximately 5 fold when PBMC were incubated for 48 hrs in the presence of PHA (1 μg/ml) or TPA (10 μg/ml). This increase in surface density is less than increases in molecules such as CD4 and CD8 (10 fold) when stimulated in a similar manner, although the comparison is based upon fluorescence. Klutzman and Gluckman (1986, Immunol. Today 7:291) have suggested that HIV binding occurs with both high and low affinity and that the high affinity binding, which represents perhaps 10% of HIV binding, leads to productive infection. The high affinity binding may require the interaction of HIV with CD4 in addition to binding to a receptor for CS3. Thus, cell killing or infection may be blocked if this interaction is prevented.

We tested this possibility by evaluating the ability of CS3-HSA to inhibit HIV mediated killing of RH9 cells following infection at a low multiplicity of infection (FIG. 3). CS3-HSA completely prevented HIV-mediated cell killing of RH9 cells in a dose range of 0.5 to 5 μg/ml. Some enhancement of RH9 cell growth was noted in some experiments when CS3-HSA was incubated with RH9 cells in the absence of HIV, although this was not a reproducible observation. An irrelevant peptide conjugate, DC7-HSA, did not protect against HIV mediated cell killing at similar doses. This suggests that disruption of HIV binding to the CS3 receptor prevents cell killing, although we can not formally rule out the possibility that CS3-HSA prevents cell killing by some other mechanism. Protection from cell killing was demonstrated at concentrations of C-CS3-HSA (0.5 μg/ml) that showed little binding by fluorescence (10%). The reason for this is unknown, but it is possible that both a high and low affinity form of the CS3 receptor exist.

One interpretation of these results is that HIV occupies the CS3 receptor but is prevented from doing so in the presence of CS3-HSA. Thus, one possibility is that crosslinking of CD4 and the CS3 receptor by HIV may be a requirement for cell killing. Further investigation is needed to explore binding, internalization and replication of HIV.

8. EXAMPLE: CHARACTERIZATION OF THE CS3 RECEPTOR

8.1. Materials and Methods

Membrane cross linking of CS3-HSA to RH9 cell surface was carried out as described (Tsudo et al., 1986, Proc. Natl. Acad. Sci. U.S.A. 83:9694–9698) with some modifications. Briefly, $5\times10^5$ RH9 cells were incubated with 5 μg $^{125}$I-CS3-HSA ($3.2\times10^6$ cpm/μg) with (FIG. 4B) or without (FIG. 4A) 100×cold CS3-HSA as competing agent for 2 hrs. at 4° C., in a final volume of 1 ml, in RPMI medium containing 10% FCS and 25 mM HEPES. The cells were pelleted (500 g×6 min.), and resuspended in 250 μl of PBS with (FIG. 4A, 4B, and 4D) or without (FIG. 4C) 0.5 mM disuccinimidyl suberate (DSS) (Pierce). After incubation for 15 min. at room temperature the cells were pelleted and resuspended in 50 μl of lysis buffer (PBS containing 1% Triton-X 100 and 1 mM PMSF). After centrifugation (10, 000g×4 min.) aliquots of supernatants ($2\times10^5$ cell equivalents) were subjected to SDS PAGE. X-OMAT film (Kodak) was exposed overnight to the dried gel. The irrelevant peptide conjugate $^{125}$I-DC7-HSA was also used for crosslinking (FIG. 4D).

8.2. Results and Discussion

The nature of the putative receptor for CS3 was investigated by crosslinking CS3-HSA to its receptor using a chemical crosslinking agent (DSS) (FIG. 4). CS3-HSA was labelled with $^{125}$I, then crosslinked to RH9 cells (Tsudo et al., supra). After disruption of the cells and running equivalent aliquots of the lysate on SDS-PAGE, autoradiography revealed a complex of CS3-HSA and receptor (CS3-HSA-R) at 108 kd (FIG. 4A) on SDS-PAGE. Competition with unlabelled CS3-HSA eliminated the complex and most of the free $^{125}$I-CS3-HSA (FIG. 4B). Conversely, only free $^{125}$I-CS3-HSA appeared in the absence of DSS crosslinker at a molecular size of 64 kd. The addition of CS3 to HSA did not alter its apparent molecular size on SDS gels. Thus, addition of CS3 peptides to the side chains of HSA did not significantly alter the stokes radius of the denatured HSA molecule. In contrast, DC7-HSA, did not crosslink to an detectable cell surface molecule in the presence of DSS (FIG. 4D) nor did it compete for binding in flow cytometry experiments (FIG. 2). The apparent molecular size of DC7-HSA on SDS gels was similar to that of CS3-HSA. Thus, the putative receptor for CS3 is a molecule with a minimum subunit size of approximately 44 kd, determined by subtraction of the apparent molecular weight of the complex from CS3-HSA (108–64 kd).

The importance of the CS3 peptide portion of HIV in the pathobiology of HIV in patients with AIDS needs to be addressed. Antibodies from HIV seropositive but asymptomatic individuals recognize CS3 in ELISA assays (Klasse et al., 1988, Proc. Natl. Acad. Sci. U.S.A. 85:5225). In contrast, most seropositive individuals with symptoms related to ARC or AIDS were unreactive to this peptide sequence. The inverse relationship of CS3 specific antibody to disease progression is suggestive, but unproven. Progressive loss of anti-CS3 antibody might lead to a greater frequency of HIV mediated cell killing and subsequent loss of CD4 cells.

HIV appears to utilize a number of mechanisms to kill cells (H. Temin, Rev. Inf. Dis., 10, 399 (1988); R. F. Garry, AIDS, in press). A TM carboxyl terminus mutant, eliminating 177–200 base pairs from the gp41 gene, retained the ability to induce cell-cell fusion, but was attenuated in its ability to kill single cells (A. G. Fisher, et al., Science 233, 655, 1986), Thus, regions of TM other than those encoding CS3 may be important in cytopathology. Our results suggest that HIV interaction with the CS3 receptor may be required for cell killing. In addition, we have shown that CS3 peptide competes with HIV for binding to CD4+ cells. Alternatively, internalization of HIV may play a role in cell lysis and blocking of the CS3 receptor may prevent internalization by blocking high-affinity binding. These and other possibilities remain to be addressed. The development of peptide analogs with high affinity for the CS3 receptor of the elicitation of neutralizing antibody to prevent HIV interaction with the CS3 receptor may be important therapeutic modalities for the treatment of AIDS.

9. EXAMPLE: CS3-HSA BLOCKS INFECTION BY HIV

9.1. Materials and Methods

Antibodies directed toward CS3 were prepared by passing anti-HIV immunoglobulin (plasma from an HIV-seropositive patient) through a protein G affinity column (Pierce Chemicals), and then passing the resulting IgG over an affinity column in which 2.5/ml mg CS3 had been immobilized onto diaminodipropylamine-agarose (Pierce Chemicals). The flow through from the column was repassed to ensure that all anti-CS3 specificity had been removed. The flow through was used as CS3-depleted anti-HIV IgG.

RH9 cells at a concentration of $2\times10^5$ cells/ml were exposed to either (i) medium; (ii) HIV virus alone; (iii) HIV virus in the presence of HSA at 20 μg/ml; (iv) HIV virus and CS3-HSA at 10 μg/ml; (v) HIV virus and 6.7 μg/ml antibody specific for CS3; or (vi) HIV virus and 6.7 μg/ml CS3 depleted anti-HIV IgG; for 4 hours, then washed three times in a 100× volume of HBSS. The cells were then incubated in RPMI containing 10% serum and 20 mM HEPES, at a concentration of about $5\times10^5$ cells ml, for 18 days (fresh medium was added in order to keep the cell concentration relatively constant).

HIV infection was measured in terms of expression of p24 protein, as quantitated by a standard assay (e.g. the F.D.A. approved Abbott Laboratory Assay).

9.2. Results and Discussion

CS3-HSA was observed to significantly inhibit HIV infection of RH9 cells, as measured by p24 production (FIG. 5). This inhibition was not observed when cells were exposed to virus and HSA alone. Therefore, not only is cell killing inhibited by CS3, but infection of virus is inhibited by CS3 as well. Furthermore, inhibition was achieved using 1 μg/ml CS3-HSA as well as 10 μg/ml CS3-HSA.

In addition, anti-CS3 antibody also inhibits production of p24 (FIG. 5). This correlates with clinical data which indicates that antibody specific to CS3 in HIV seropositive patients is associated with the absence of AIDS-related disease.

10. EXAMPLE: CS3 INHIBITS BINDING OF HIV TO CELLS

10.1. Materials and Methods

Aliquots of HIV strain IIIb were prepared from chronically infected [RH9] cells by centrifugation at 100,000×g. Human MOLT-4 cells were exposed to either (i) HIV virus alone or (ii) CS3-HSA at 30 μg/$10^6$ cells, followed by HIV virus. Following treatment, virus bound to the cells was detected by CS3-depleted anti-HIV IgG (prepared as described in Section 9.1, supra) and FITC-labelled $F(ab)_2$ goat anti-human IgG, followed by flow cytometry.

10.2. Results and Discussion

The mechanism of action of CS3-HSA was examined by flow cytometry. Cytopathology and HIV p24 antigen assays demonstrate that RH9 cells treated with HIV in the presence of CS3-HSA are protected from HIV mediated cytopathic effects and express significantly reduced levels of p24 antigen. These results suggest that HIV is prevented from infecting cells in the presence of CS3-HSA, but do not suggest a mechanism. Therefore, direct binding studies were performed using MOLT-4 cells which have higher CD4 expression than RH9 cells (58 vs 15%). CS3-HSA competed for the binding of HIV on MOLT-4 cells (FIG. 6). A four-fold decrease in mean fluorescence was observed by incubation of MOLT-4 cells with 20 μg CS3-HSA/$10^6$ cells prior to addition of HIV. It is possible that binding of g41 to the CS3 receptor is necessary for high affinity binding of HIV and consequent infection.

11. EXAMPLE: CS3-HSA UPREGULATES EXPRESSION OF THE CS3 RECEPTOR AND HLA-DR

11.1. Materials and Methods

To study the expression of CS3 receptor and HLA-DR on human peripheral blood mononuclear cells (PBMC) exposed to CS3-HSA, PBMC (harvested by Leucoprep®, Becton Dickinson) were incubated with c-CS3-HSA (2.5 μg/$10^{-6}$ cells) or the irrelevant peptide DC7-HSA (5 μg/$10^6$ cells) for 72 hours in RPMI containing 10% AB positive human serum. The cells were washed, and then incubated for 20 minutes at 4° C. then incubated with FITC labelled anti-CD4 (T4), FITC anti-CD 3 (T3), or FITC anti-CD2 (T11), and rhodamine C-CS3-HSA, or phycoerythrin labelled anti-CD8 (T8), and FITC C-CS3-HSA, or phycoerythrin anti-HLA-DR and FITC C-C53-HSA. The cells were then washed and analyzed on a Coulter Profile Flow Cytometer.

To measure expression of the CS3 receptor on phytohemagglutinin (PHA) or tetraphorbol 13-myristyl acetate (TPA) activated cells, PBMC were incubated at $2\times10^6$ cells/ml with PHA (1 μg/ml) or TPA (10 ng/ml) for 48 hours in RPMI with 10% AB positive human serum or with medium alone. The cells were then washed and analyzed for expression of CS3 receptor with FITC labelled C-CS3-HSA (4 μg/$10^6$ cells).

FITC labelled HSA was used to obtain control fluorescence.

11.2. Results and Discussion

The results in FIG. 7 suggest that CS3 can increase the expression of its own receptor in the absence of any mitogen or antigen stimulation. The percentage of cells expressing CS3 receptor increased as did the density of expression (two-fold). Interestingly, a 10-fold increase in the percentage of cells expressing HLA-DR was also observed. Since these cells are >90% T lymphocytes, it provides additional support for the notion that CS3 partially activates cells, probably through selective increases in intracellular signals. However, activation by mitogen in the absence of CS3 also resulted in increased CS3 receptor expression (FIG. 8). In this experiment, only the density of expression was examined following mitogen activation. Thus, the regulation of the CS3 receptor does not require complete activation (induction of DNA synthesis) in PBMC, since CS3-HSA alone does not fully activate. Treatment with CS3-HSA does enhance intracellular calcium flux suggesting partial activation only.

12. EXAMPLE: EXPRESSION OF THE CS3 RECEPTOR ON VARIOUS CELL LINES

The CS3 receptor has been identified, by flow cytometric analysis using FITC-C-CS3-HSA on a variety of cell lines, as shown in Table I.

TABLE I

Flow Cytometric Analysis Of Cell Lines For Expression Of CS3 Receptor

| Cell line | Percent Positive |
|---|---|
| jurkat (human T cell tumor) | >95 |
| RH9 (human CD4 lymphocyte tumor) | >95 |
| CTLL (murine T lymphocyte clone) | 16 |
| P815 (murine mastocytoma) | 14 |
| YAC-1 (murine hematopoietic tumor) | 0 |
| 144-2C11 (hamster × mouse hybridoma) | 26 |
| EL-4 (murine thymoma) | 0 |

13. EXAMPLE: DEVELOPMENT OF A NEW ASSAY DEMONSTRATING THE MECHANISM OF CS3 ACTION

The present invention also provides for an assay system to measure or detect HIV binding. A binding assay has been developed for viruses, particularly HIV, which has broad application for screening for antivirals (drugs, peptides and antibodies) that are potentially neutralizing by virtue of the ability to prevent binding of virus to target cells (See FIG. 12). The binding assay comprises exposing cells to virus (e.g. HIV) in medium for a period of time sufficient to allow binding of virus to cells to occur, centrifuging the cells and virus through a high specific gravity liquid such as, preferably, silicon oil, freezing the media and cell pellet, separating the cell pellet from the frozen medium, and assaying the cell pellet for viral core protein. This assay may be used to test the ability of a compound (e.g. a peptide) to block virus biding. For example, CS3-HSA may be incubated with MT4 cells prior to the addition of HIV (5–6 infectious particles per cell). Cells may then be centrifuged (preferably microfuged) through silicon oil, the tube may then be frozen (for example in liquid $N_2$) then the pellet snipped off to separate it from the frozen medium. The cell pellet may then be assayed for p24 core antigen content using, for example, the Abbott assay or any suitable HIV assay system known in the art. For its use with HIV, freezing the tube is essential to prevent any HIV from the medium from contaminating the cell pellet. Analysis of core protein is also an important feature, since gp120 from particles that do not infect would result in high backgrounds if antibody to gp120 was used. This assay may be used to identify compounds which block HIV/cell binding such as compounds which block HIV binding to the CS3 receptor.

CS3 at 10 ng/ml effectively blocks 50–60% of HIV binding and complete inhibition of binding was seen at a dose that is saturating by flow cytometry (5 μg/$10^6$ cells). The results shown in FIG. 9 are representative of five experiments. In addition, experiments indicated that when a dose range of HIV was used (without inhibitors) the binding of HIV was biphasic, consistent with a two receptor model for binding or binding by two distinct affinities.

Soluble CD4 and irrelevant peptide conjugates were used as positive and negative controls, respectively. While DC7-HSA did not affect HIV binding, sCD4 was effective. However, high concentrations of sCD4 resulted in diminished blocking of HIV infection (FIG. 9). At high concentrations of sCD4, gp120 may be lost by the virus. The results suggest that, if this is the case, greater binding of HIV results, probably from exposure of gp41 which would be more readily available to bind to its cellular receptor. Further support of this hypothesis was obtained by treatment of virus with sCD4 and cells with CS3-HSA. In this case their combination was more effective that sCS4 alone at the higher concentration (10ng/ml), resulting in a further reduction of HIV binding (Abs=05 with both and Abs=15 with sCD4 alone).

13.1. Effects of the CS3 Peptide on HIV Pathogenesis

It was important to demonstrate that the ability to block cell killing and infection with CS3-HSA extends to other cell lines and other isolates of HIV. Experiments with human PBMC demonstrated that cell killing is blocked by CS3-HSA. Extensive studies measuring both cell killing and infection have been performed using the MT4 and MOLT4 cells and the $HIV_{IIB}$.$HIV_{RE}$ and $HIV_{HITI}$ isolates. Representative results are shown in FIG. 10.

Investigation of the effect of the CS3 peptide on cell killing and infection have been performed. Incubation of $CD4^+$ cells with HIV in the presence of CS3-HSA abrogated HIV-mediated cytopathicity (FIG. 10) and inhibited HIV infection (FIG. 8).

In summary, we have shown that the ability of HIV to kill and infect $CD4^+$ cells can be inhibited by interfering with HIV binding to the receptor for gp41 (TM). The CS3 peptide is the CS3 receptor (also known as the TM receptor) domain which appears to be a major determinant for binding specificity.

These results demonstrate that 1. the ability of CS3-HSA to block cell killing and infection can be consistently demonstrated in all cell lines tested (MT4, RH9 and MOLT4).
2. CS3-HSA can block the cell killing and infection by all HIV Isolates examined. This is consistent with the conserved nature of the CS3 sequence in HIV isolates (Los Alamos data base).

13.2. Distribution of the CS3 Binding Domain

Further analysis was performed with monoclonals to T cells (antibodies to CD4, CD8, and CD2, Coulter), B cells (B4, Coulter), and monocytes (MO1 and MO2, Coulter) in double staining with CS3-HSA. Rhodamine showed that lymphocytes and monocytes were positive for CS3 binding (Table II). In addition, a neuroblastoma cell line, SK-NMC, recently reported to harbor HIV after exposure to the virus expresses the CS3 (TM) receptor, as determined by immunofluorescent microscopy. Coupled with the demonstration that the CS3 (TM) receptor is expressed on cells of the monocyte lineage, these data suggest that infection of these cell types may be mediated through the CS3 receptor.

13.3. Regulation of CS3 Binding Domain Expression

The regulation of the level of CS3 receptor on the cell surface was also examined. PBMC were activated then analyzed for total expression of CS3 receptor. When PBMC were activated for 2 days with PHA or TPA (mitogens that activate lymphocytes) receptor density increased by 5–8 fold compared to cultures without PHA (FIG. 11). Thus, activation of lymphocytes increased receptor density, suggesting that activated cells may be more susceptible to infection and cytopathicity or syncytium, since the CS3 (TM) receptor mediated these effects of HIV.

One important conclusion can also be drawn. Experiments with PBMC and CD4 cell lines (FIG. 11) with TPA demonstrate that CD4 loss from the cell surface was not accompanied by loss of CS3 binding. In fact, the relationship is inverse. Thus, expression of the CS3 binding domain appeared to be independent from CD4.

TABLE II

EXPRESSION OF CS3 RECEPTOR ON PERIPHERAL BLOOD MONONUCLEAR CELLS

| Cell Subset | % Expressing CS3 Receptor |
|---|---|
| CD4 | 90* |
| CD2 | 90 |
| HLA-DR | 90 |
| MO1 | 87 |
| MO2 | 87 |
| CD8 | 60 |

*Dual fluorescence flow cytometry was used to determine the percentage of each subset positive for expression of CS3, using CS3-HSA-Rhodamine or FITC. Subset markers were monoclonal antibodies from Coulter as follows: T cells, T4 for helper, T8 for suppressor cytotoxic, T11 for pan T cells, 12 for HLA-DR, MO1 and MO2 for monocyte/macrophage.

RH9 cells have been stimulated with antibody to CD3 or with TPA or incubated in medium alone. We examined both CD4 and CS3-HSA binding (FIG. 11). As expected CD4 was lost upon treatment with TPA; however, CS3 binding was increased. Stimulation with antibody to CD3 resulted in a time dependent increase in receptor density. Interestingly, control cultures demonstrated variation in CD4 expression which is probably related to cell cycle and division (MOLT 4 and MT do not express CD3, so anti-CD3 stimulation was not attempted).

Additional studies with MT4, MOLT4 cells have been performed to investigate CS3 binding with respect to time of treatment with PHA or TPA. Similar results have been obtained confirming independent regulation of CD4 and CS3 domain expression.

These studies revealed:

1. There was no relationship between expression of CD4 and CS3 domain(s).
2. Expression of the CS3 binding domain can be regulated in a fashion that may be dependent on the activating agent and cell. Thus, there may be specificity to regulation of the CS3 domain via distinct signal transduction pathways.

Regarding the numbers of CS3 receptors flow cytometry results suggest that there are <10,000 receptors per cell for CS3-HSA, which compares well with Skatchard results. The binding demonstrated excellent specificity for CS3 and not irrelevant peptide.

14. EXAMPLE: THE CS3 RECEPTOR COMPRISES TWO POLYPEPTIDE SUBUNITS

The crosslinking of radiolabelled CS3 to the surface of RH9 cells revealed polypeptides of approximately 45 and 95 kd indicating that the CS3 receptor may comprise two polypeptide subunits. Specificity was demonstrated by cold competition with CCS3 and CCS3-HSA. However, another unrelated peptide containing a domain of the CD4 binding site of gp120 also competed at these concentrations. Several possibilities would explain this result. First, high concentrations of most hydrophobic and particularly amphipathic peptides tend to alter the structure and fluidity of plasma membranes. Second, there does appear to be a relationship between the expression of the CS3 receptor and CD4 on cells that express both. Flow cytometry results suggest that in double positive cells, treatment with phorbol esters results in a down regulation of both receptors. However, it is clear that these receptors are not identical based upon characterization of the polypeptides through crosslinking studies and distribution studies which demonstrate that the CS3 receptor is expressed on cells that do not express CD4.

The present invention is not to be limited in scope by the specific embodiments described herein. Indeed, various modifications of the invention in addition to those described herein will become apparent to those skilled in the art from the foregoing description and accompanying figure. Such modifications are intended to fall within the scope of the claims. Various publications are cited herein, the disclosures of which are incorporated by reference in their entireties.

What is claimed:

1. A substantially purified protein comprising a CS3 receptor protein which binds to the peptide LQARILAVERYLKDQQL.

2. The substantially purified protein of claim 1 which has a molecular weight of approximately 108 kd when bound to $^{125}$I-CS3-HSA.

3. The substantially purified protein of claim 1 which comprises a protein subunit with a molecular weight of about 43–47 kd.

4. A substantially purified CS3 receptor protein which binds to a peptide having the sequence LQARILAVERYLKDQQL, and which has two subunits, namely (i) a lower molecular weight subunit having a molecular weight of about 43–47 KD; and (ii) a higher molecular weight subunit.

5. A substantially purified protein which is the higher molecular weight subunit of the CS3 receptor protein of claim 4.

* * * * *

UNITED STATES PATENT AND TRADEMARK OFFICE

CERTIFICATE OF CORRECTION

PATENT NO. : 5,567,805

DATED : September 7, 1994

INVENTOR(S) : Henderson et al

It is certified that error appears in the above-indentified patent and that said Letters Patent is hereby corrected as shown below:

On the title page:

Item 56, line 12, "Sci." should read --Sci. USA--;

Col. 1, delete lines 13-55;

Col. 11, line 43, "FIG. 13" should read --FIG. 12--;

Col. 11, line 51, "biding" should read --binding--;

Col. 12, line 18, "cells/mi" should read --cells/ml--;

UNITED STATES PATENT AND TRADEMARK OFFICE

CERTIFICATE OF CORRECTION

PATENT NO. : 5,567,805 — Page 2 of 2

DATED : September 7, 1994

INVENTOR(S) : Henderson et al

It is certified that error appears in the above-indentified patent and that said Letters Patent is hereby corrected as shown below:

Col. 15, line 23, "through a" should read --through A--;

Col. 17, line 47, "biding" should read --binding--;

Col. 18, line 15, "that" should read --than--;

Col. 18, line 27, "$^{HIV}$IIB" should read --$^{HIV}$IIIB--;

Signed and Sealed this

First Day of April, 1997

Attest:

BRUCE LEHMAN

Attesting Officer

*Commissioner of Patents and Trademarks*